US010252071B2

(12) United States Patent
Cao et al.

(10) Patent No.: US 10,252,071 B2
(45) Date of Patent: Apr. 9, 2019

(54) MULTI-THRESHOLD SENSING OF CARDIAC ELECTRICAL SIGNALS IN AN EXTRACARDIOVASCULAR IMPLANTABLE CARDIOVERTER DEFIBRILLATOR

(71) Applicant: Medtronic, Inc., Minneapolis, MN (US)

(72) Inventors: Jian Cao, Shoreview, MN (US); Timothy A. Ebeling, Circle Pines, MN (US); Saul E. Greenhut, Aurora, CO (US); Michael W. Heinks, New Brighton, MN (US); Irving J. Sanchez, Blaine, MN (US); Paul R. Solheim, Blaine, MN (US); Xusheng Zhang, Shoreview, MN (US); Gerald P. Arne, Wayzata, MN (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 15/142,171

(22) Filed: Apr. 29, 2016

(65) Prior Publication Data
US 2017/0312534 A1 Nov. 2, 2017

(51) Int. Cl.
*A61N 1/39* (2006.01)
*A61N 1/05* (2006.01)
(Continued)

(52) U.S. Cl.
CPC .......... *A61N 1/3987* (2013.01); *A61B 5/0456* (2013.01); *A61N 1/05* (2013.01);
(Continued)

(58) Field of Classification Search
CPC ...... A61N 1/3987; A61N 1/05; A61N 1/3956; A61N 1/3925; A61N 1/365; A61N 1/3621; A61N 1/39; A61B 5/0456
See application file for complete search history.

(56) References Cited

U.S. PATENT DOCUMENTS

| 5,312,441 A | 5/1994 | Mader et al. |
| 5,354,316 A | 10/1994 | Keimel |

(Continued)

OTHER PUBLICATIONS (PCT/US2017/029762) PCT Notification of Transmittal of the International Search Report and the Written Opinion of the International Searching Authority, dated Jul. 31, 2017, 11 pages.
(Continued)

*Primary Examiner* — Rex R Holmes

(57) ABSTRACT

An implantable medical device system capable of sensing cardiac electrical signals includes a sensing circuit, a therapy delivery circuit and a control circuit. The sensing circuit is configured to receive a cardiac electrical signal and sense a cardiac event in response to the signal crossing a cardiac event sensing threshold. The therapy delivery circuit is configured to deliver an electrical stimulation therapy to a patient's heart via the electrodes coupled to the implantable medical device. The control circuit is configured to control the sensing circuit to set a starting value of the cardiac event sensing threshold and hold the starting value constant for a sense delay interval. The control circuit is further configured to detect an arrhythmia based on cardiac events sensed by the sensing circuit and control the therapy delivery circuit to deliver the electrical stimulation therapy in response to detecting the arrhythmia.

29 Claims, 16 Drawing Sheets

(51) Int. Cl.
*A61B 5/0456* (2006.01)
*A61N 1/362* (2006.01)
*A61N 1/365* (2006.01)

(52) U.S. Cl.
CPC ......... *A61N 1/3925* (2013.01); *A61N 1/3956* (2013.01); *A61N 1/365* (2013.01); *A61N 1/3621* (2013.01); *A61N 1/39* (2013.01)

(56) References Cited

U.S. PATENT DOCUMENTS

| | | | |
|---|---|---|---|
| 5,545,186 A | 8/1996 | Olson et al. | |
| 5,620,466 A | 4/1997 | Haefner et al. | |
| 5,709,215 A | 1/1998 | Perttu et al. | |
| 5,800,466 A | 9/1998 | Routh et al. | |
| 5,957,857 A | 9/1999 | Hartley | |
| 6,249,701 B1 | 6/2001 | Rajasekhar et al. | |
| 6,393,316 B1 | 5/2002 | Gillberg et al. | |
| 6,459,937 B1 | 10/2002 | Morgan et al. | |
| 6,526,311 B2 | 2/2003 | Begemann | |
| 6,539,259 B1 | 3/2003 | Weinberg et al. | |
| 6,862,476 B2 | 3/2005 | Mouchawar et al. | |
| 7,027,858 B2 | 4/2006 | Cao et al. | |
| 7,031,771 B2 | 4/2006 | Brown et al. | |
| 7,330,757 B2 | 2/2008 | Ostroff et al. | |
| 7,333,855 B2 | 2/2008 | Gunderson et al. | |
| 7,444,182 B2 | 10/2008 | Ostroff et al. | |
| 7,463,926 B1 | 12/2008 | Levine et al. | |
| 7,496,409 B2 | 2/2009 | Greenhut et al. | |
| 7,761,150 B2 | 7/2010 | Ghanem et al. | |
| 7,783,354 B2 | 8/2010 | Gunderson | |
| 7,831,304 B2 | 11/2010 | Cao et al. | |
| 7,937,135 B2 | 5/2011 | Ghanem et al. | |
| 7,970,473 B2 | 6/2011 | Nabutovsky et al. | |
| 8,050,754 B2 | 11/2011 | Ostroff et al. | |
| 8,055,342 B2 | 11/2011 | Zhang et al. | |
| 8,160,684 B2 | 4/2012 | Ghanem et al. | |
| 8,386,024 B2 | 2/2013 | Gunderson et al. | |
| 8,437,842 B2 | 5/2013 | Zhang et al. | |
| 8,626,280 B2 | 1/2014 | Allavatam et al. | |
| 8,694,097 B2 | 4/2014 | Cao et al. | |
| 8,744,555 B2 | 6/2014 | Allavatam et al. | |
| 8,886,296 B2 | 11/2014 | Patel | |
| 8,914,106 B2 | 12/2014 | Charlton et al. | |
| 8,942,795 B2 | 1/2015 | Gunderson et al. | |
| 8,942,802 B2 | 1/2015 | Ostroff et al. | |
| 8,965,491 B2 | 2/2015 | Allavatam et al. | |
| 8,983,586 B2 | 3/2015 | Zhang | |
| 9,002,443 B2 | 4/2015 | Zhang et al. | |
| 9,155,485 B2 | 10/2015 | Ostroff et al. | |
| 9,956,423 B2 * | 5/2018 | Zhang | A61N 1/3987 |
| 2004/0049120 A1 | 3/2004 | Cao et al. | |
| 2008/0161870 A1 | 7/2008 | Gunderson | |
| 2012/0109240 A1 | 5/2012 | Zhou et al. | |
| 2015/0105680 A1 | 4/2015 | Ostroff et al. | |
| 2015/0306375 A1 | 10/2015 | Marshall et al. | |
| 2015/0306410 A1 | 10/2015 | Marshall et al. | |
| 2016/0001090 A1 | 1/2016 | Ostroff et al. | |

OTHER PUBLICATIONS

Swerdlow et al., "Advanced ICD Troubleshooting: Part 1", Pace, vol. 28, Dec. 2005, 25 pages.
Zhang et al, "System and Method for Sensing and Detection in an Extra-Cardiovascular Implantable Cardioverter Defibrillator", U.S. Appl. No. 15/140,802, filed Apr. 27, 2016, 77 pages.
Zhang et al., "Method and Apparatus for Beat Acquisition During Template Generation in a Medical Device Having Dual Sensing Vectors", U.S. Appl. No. 14/604,260, filed Jan. 23, 2015, 75 pages.
Zhang et al., "Method and Apparatus for Beat Acquisition During Template Generation in a Medical Device Having Dual Sensing Vectors", U.S. Appl. No. 15/002,521, filed Jan. 21, 2016, 80 pages.
Cao et al., "T-Wave Oversensing Rejection", U.S. Appl. No. 14/705,010, filed May 6, 2015, 50 pages.
Marshall et al., "Extravascular Implantable Electrical Lead Having Undulating Configuration", U.S. Appl. No. 14/963,303, filed Dec. 9, 2015, 44 pages.

* cited by examiner

MULTI-THRESHOLD SENSING OF CARDIAC ELECTRICAL SIGNALS IN AN EXTRACARDIOVASCULAR IMPLANTABLE CARDIOVERTER DEFIBRILLATOR

TECHNICAL FIELD

The disclosure relates generally to an extra-cardiovascular implantable cardioverter defibrillator (ICD) system, device and method for sensing cardiac electrical signals using extra-cardiovascular electrodes.

BACKGROUND

Medical devices, such as cardiac pacemakers and ICDs, provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves. In other examples, a non-transvenous lead may be coupled to the ICD, in which case cardiac signal sensing presents new challenges in accurately sensing cardiac electrical events.

SUMMARY

In general, the disclosure is directed to techniques for controlling a cardiac event sensing threshold by a medical device. The cardiac event sensing threshold may be an R-wave sensing threshold controlled by the medical device to avoid oversensing of T-waves and P-waves while maintaining high sensitivity for detecting ventricular tachyarrhythmia. In some examples, the medical device is an ICD coupled to an extra-cardiovascular lead carrying at least one sensing electrode.

In one example, the disclosure provides a system comprising an implantable medical device for sensing cardiac electrical events. The system includes a sensing circuit, a therapy delivery circuit and a control circuit. The sensing circuit is configured to receive a cardiac electrical signal from electrodes coupled to the implantable medical device and sense a cardiac event attendant to a myocardial depolarization in response to the cardiac electrical signal crossing a cardiac event sensing threshold. The therapy delivery circuit is configured to deliver an electrical stimulation therapy to a patient's heart via the electrodes coupled to the implantable medical device. The control circuit is configured to determine a gain based on a minimum threshold value of the cardiac event sensing threshold, determine a maximum limit of a starting threshold value based on the gain and the minimum threshold value, and control the sensing circuit to set a starting value of the cardiac event sensing threshold to be equal to or less than the maximum limit. The control circuit is further configured to detect an arrhythmia based on cardiac events sensed by the sensing circuit and control the therapy delivery circuit to deliver the electrical stimulation therapy in response to detecting the arrhythmia.

In another example, the disclosure provides a method performed by a system including an implantable medical device for sensing cardiac electrical signals. The method includes receiving a cardiac electrical signal by a sensing circuit of the implantable medical device via electrodes coupled to the implantable medical device; setting a cardiac event sensing threshold to a starting threshold value; sensing a cardiac event attendant to a myocardial depolarization in response to the cardiac electrical signal crossing the cardiac event sensing threshold; detecting an arrhythmia based on a plurality of cardiac events sensed by the sensing circuit; and controlling a therapy delivery circuit to deliver an electrical stimulation therapy in response to detecting the arrhythmia. Setting the starting threshold value includes determining by a control circuit of the implantable medical device a gain based on a minimum threshold value of the cardiac event sensing threshold, determining a maximum limit of the starting threshold value based on the gain and the minimum threshold value, and setting the starting value of the cardiac event sensing threshold to be equal to or less than the maximum limit.

In another example, the disclosure provides a non-transitory, computer-readable storage medium comprising a set of instructions which, when executed by a processor of an implantable medical device, cause the system to set a cardiac event sensing threshold to a starting threshold value; sense a cardiac event attendant to a myocardial depolarization by a sensing circuit of the implantable medical device in response to a cardiac electrical signal crossing the cardiac event sensing threshold; detect an arrhythmia based on a plurality of cardiac events sensed by the sensing circuit; and control a therapy delivery circuit of the implantable medical device to deliver the electrical stimulation therapy in response to detecting the arrhythmia. Setting the cardiac event sensing threshold to the starting threshold value comprises determining a gain based on a minimum threshold value of the cardiac event sensing threshold, determining a maximum limit of the starting threshold value based on the gain and the minimum threshold value; and setting the starting value of the cardiac event sensing threshold to be equal to or less than the maximum limit.

In yet another example the disclosure provides a system comprising an implantable medical device for sensing cardiac electrical events including a sensing circuit, a therapy delivery circuit and a control circuit. The sensing circuit is configured to receive a cardiac electrical signal from electrodes coupled to the implantable medical device and sense a cardiac event attendant to a myocardial depolarization in response to the cardiac electrical signal crossing a cardiac event sensing threshold. The therapy delivery circuit configured to deliver an electrical stimulation therapy to a patient's heart via the electrodes coupled to the implantable medical device. The control circuit is configured to control the sensing circuit to: set the cardiac event sensing threshold to a starting value; hold the cardiac event sensing threshold constant at the starting value for a sense delay interval; adjust the cardiac event sensing threshold to a second threshold value upon expiration of the sense delay interval;

and hold the cardiac event sensing threshold constant at the second threshold value for a drop time interval. The control circuit is further configured to detect an arrhythmia based on a plurality of cardiac events sensed by the sensing circuit; and control the therapy delivery circuit to deliver the electrical stimulation therapy in response to detecting the arrhythmia.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for sensing cardiac electrical signals using implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for reliably sensing R-waves, attendant to ventricular depolarization, using extra-cardiovascular electrodes by applying multiple sensing thresholds to avoid oversensing of T-waves attendant to ventricular repolarization and P-waves attendant to atrial depolarization.

The techniques are described in conjunction with an implantable medical lead carrying extra-cardiovascular electrodes, but aspects disclosed herein may be utilized in conjunction with other cardiac electrical sensing lead and electrode systems. For example, the techniques for controlling an R-wave sensing threshold as described in conjunction with the accompanying drawings may be implemented in any implantable or external medical device enabled for sensing cardiac electrical signals, including implantable pacemakers, ICDs or cardiac monitors coupled to transvenous or epicardial leads carrying sensing electrodes; leadless pacemakers, ICDs or cardiac monitors having housing-based sensing electrodes; and external pacemakers, defibrillators, or cardiac monitors coupled to external, surface or skin electrodes.

Figure 1A:
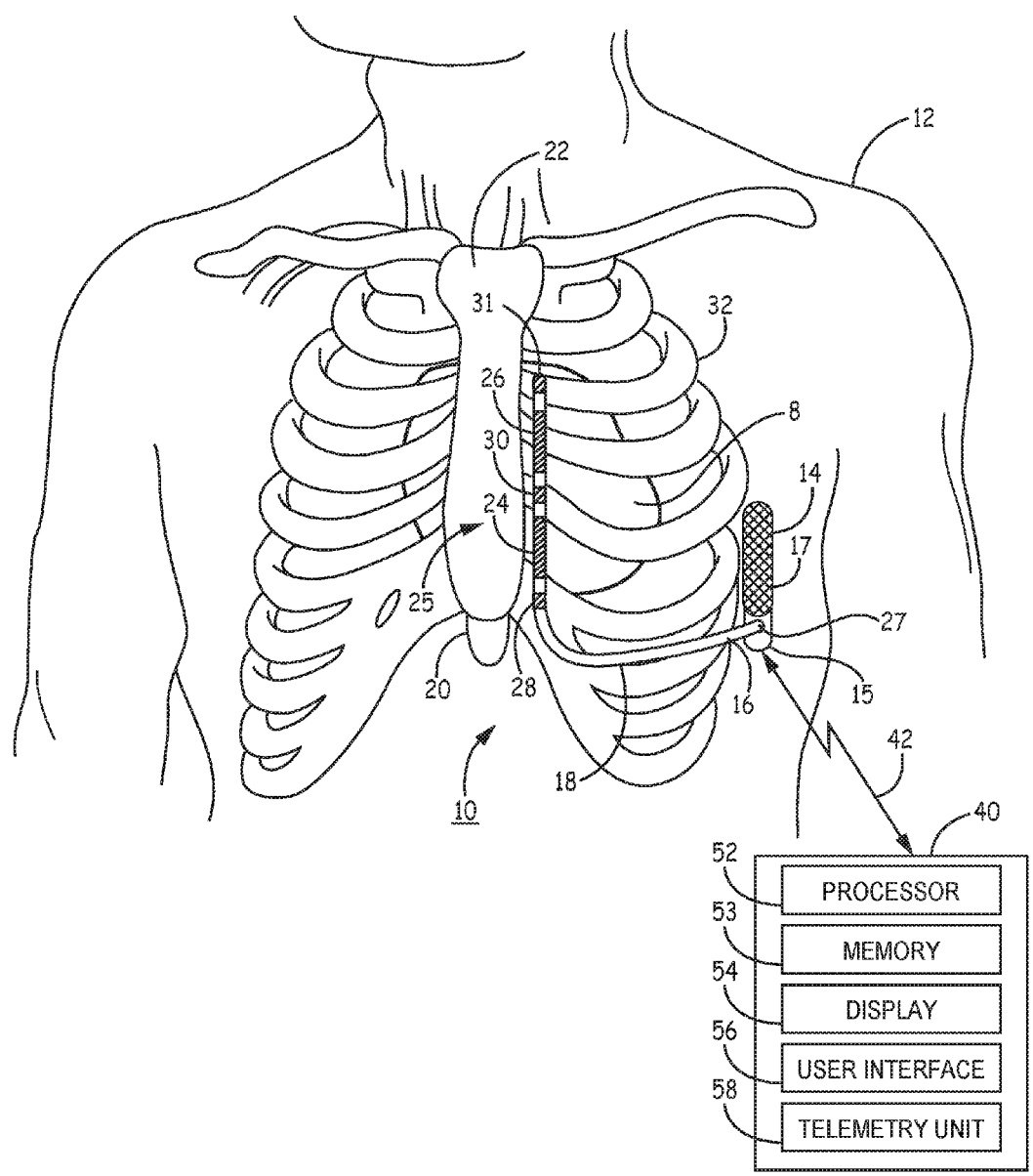
FIGS. 1A and 1B are conceptual diagrams of an extra-cardiovascular ICD system according to one example.
Figure 1B:
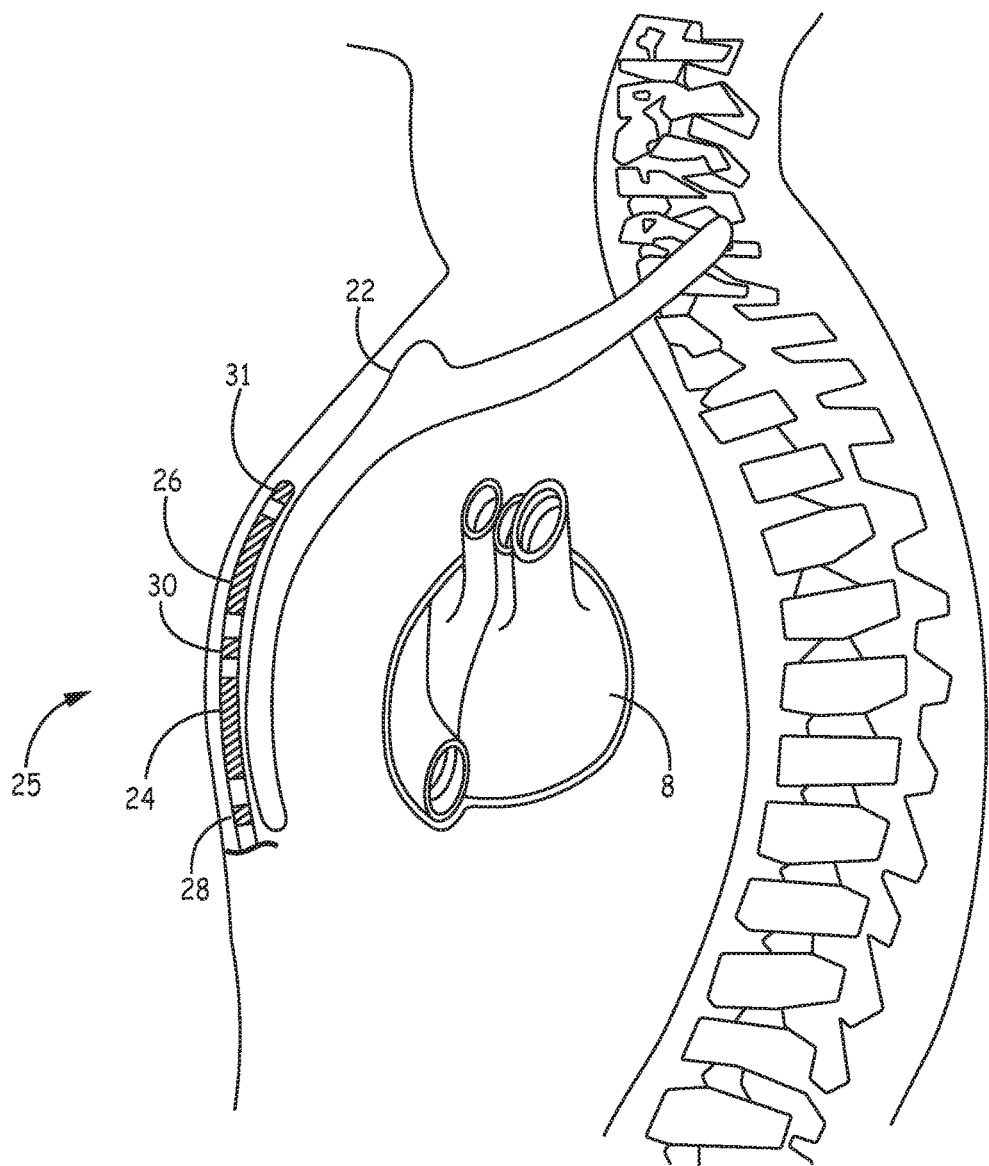

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a can electrode). In examples described herein, housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, sensors, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. Electrodes 24 and 26 may be used in a pacing electrode vector for delivering extra-cardiovascular pacing pulses such as anti-tachycardia pacing (ATP) pulses or bradycardia pacing pulses and/or in a sensing vector used to sense cardiac electrical signals and detect ventricular tachycardia (VT) and ventricular fibrillation (VF).

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31. Each of pacing and sensing electrodes 28, 30 and 31 are coupled to respective electrical conductors, which may be separate respective conductors within the lead body. The respective conductors electrically couple the electrodes 24, 26, 28, 30 and 31 to circuitry, such as a therapy circuit and/or a sensing circuit, of ICD 14 via connections in the connector assembly 17, including associated electrical feedthroughs crossing housing 15. The electrical conductors transmit therapy from a therapy circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. In one example, cardiac electrical signals are sensed between pace/sense electrodes 28 and 30, and ATP pulses (or other cardiac pacing pulses) are delivered between pace/sense electrode 30 used as a cathode electrode and defibrillation electrode 24 used as a return anode electrode. In other examples, cardiac pacing pulses may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and cardiac pacing electrode vectors may be selected according to individual patient need.

If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the extra-cardiovascular pacing techniques disclosed herein are described in U.S. Publication No. 2015/0306375 (Marshall, et al.) and U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14. For example, as described in conjunction with FIGS. 10 and 11, a clinician may view cardiac electrical signals received from ICD 14 during VF induction for testing programmed sensitivity settings and during normal sinus rhythm for reviewing and selecting programmable R-wave sensing threshold parameter settings.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling an R-wave sensing threshold as described herein. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used to control the R-wave sensing threshold according to techniques disclosed herein may be programmed into ICD 14 using external device 40.

Figure 2A:
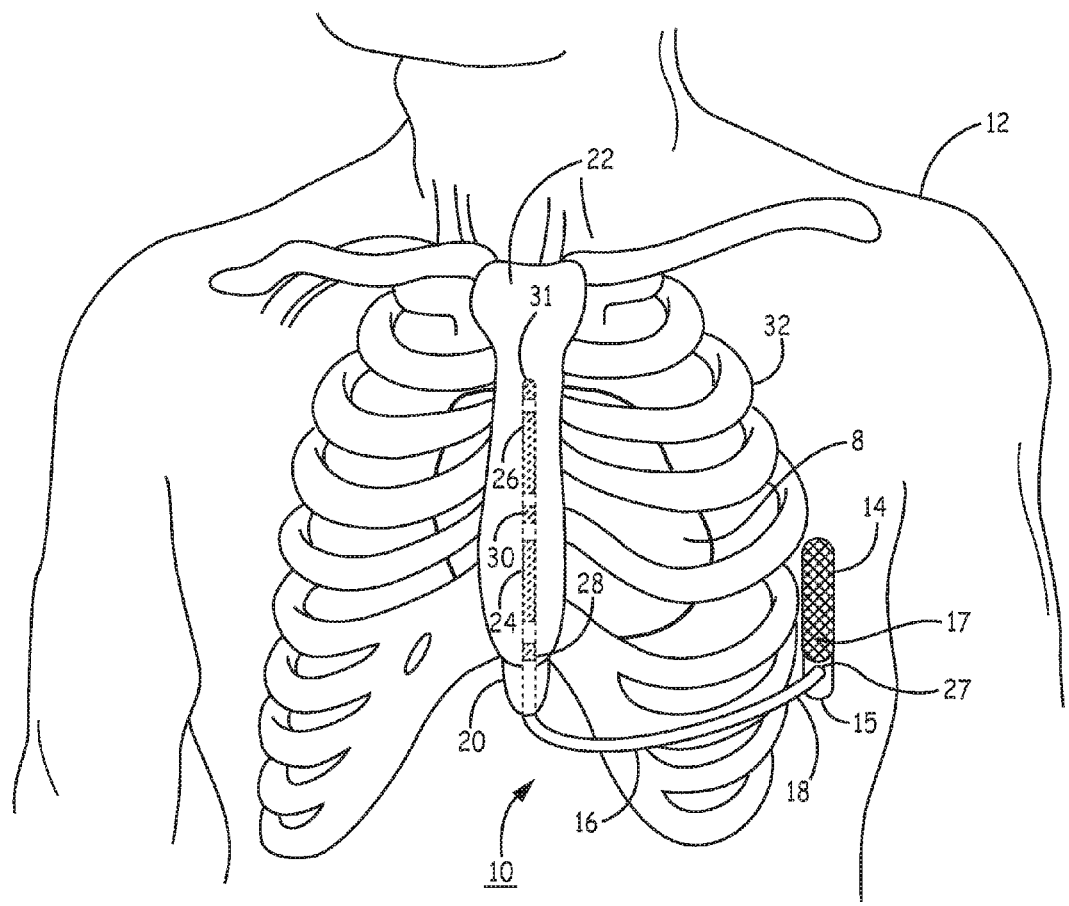
FIGS. 2A-2C are conceptual diagrams of a patient implanted with the extra-cardiovascular ICD system of FIG. 1A in a different implant configuration.
Figure 2B:
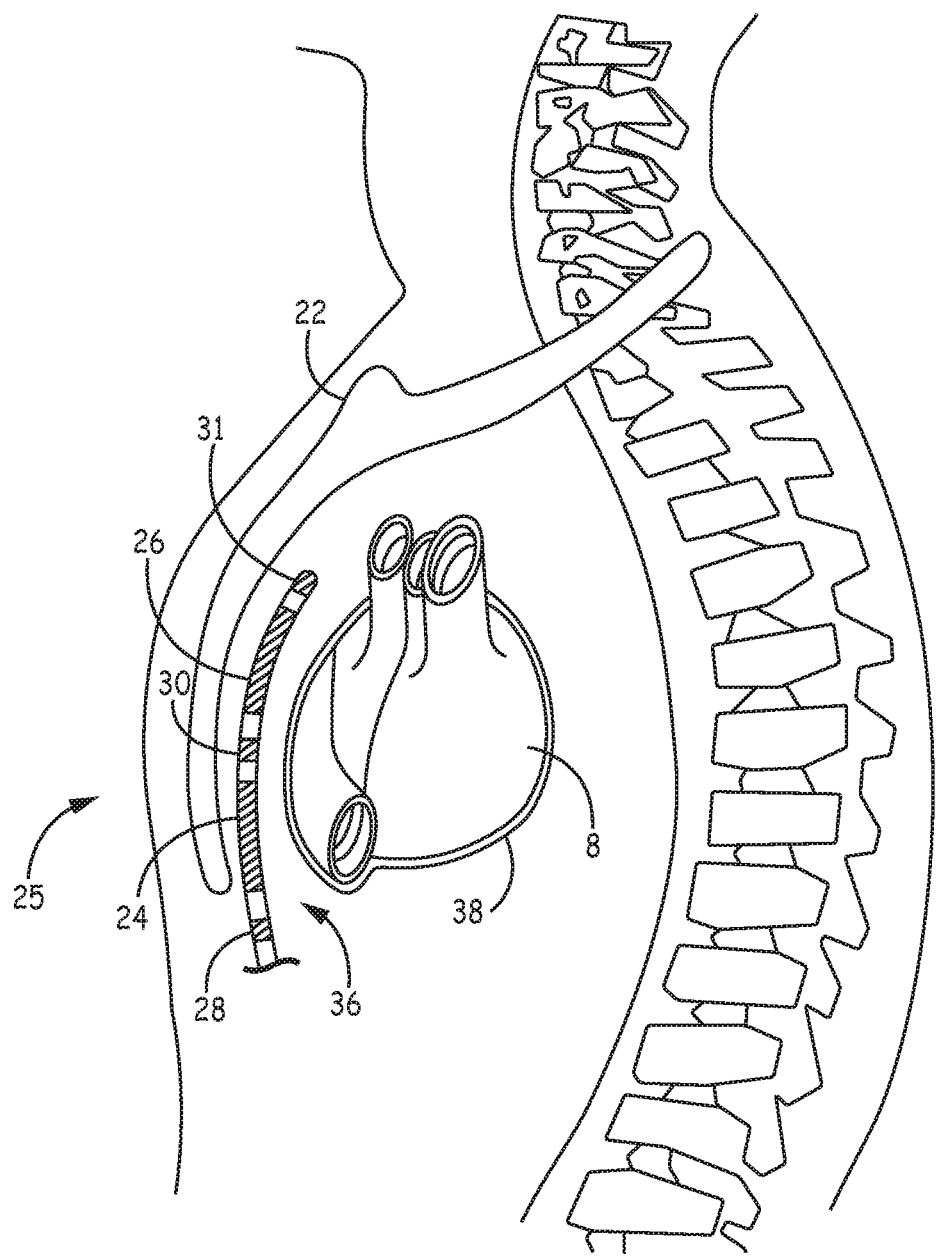
Figure 2C:
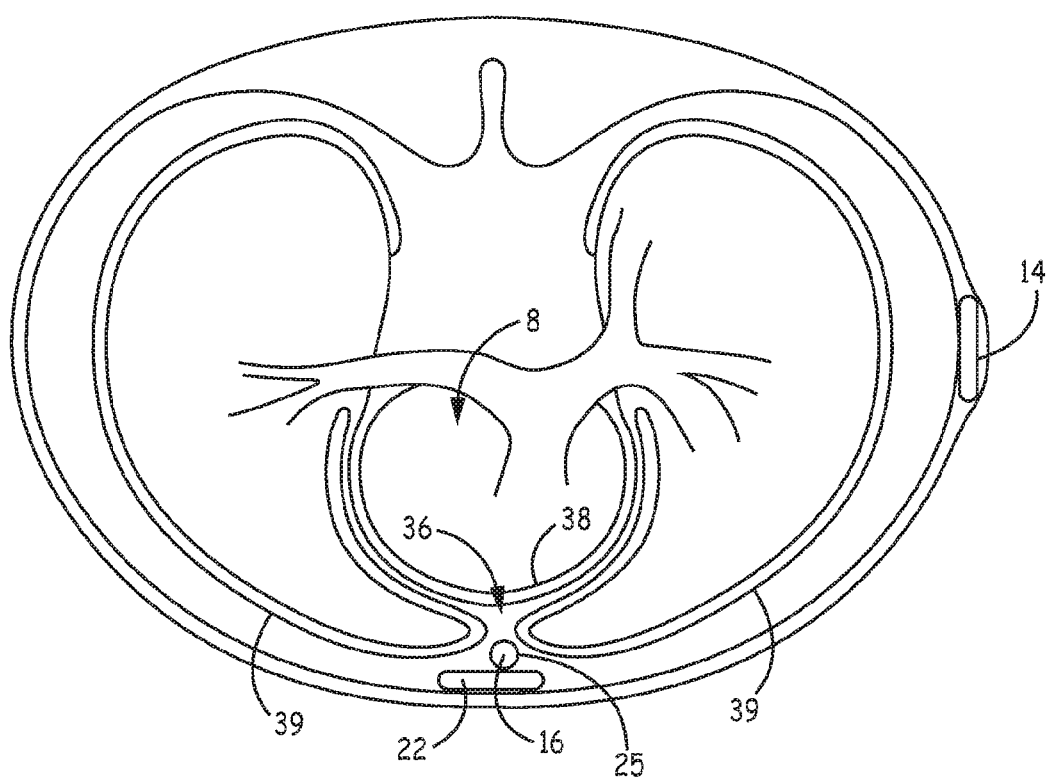

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the techniques described herein are generally disclosed in the above-incorporated patent applications.

Figure 3:
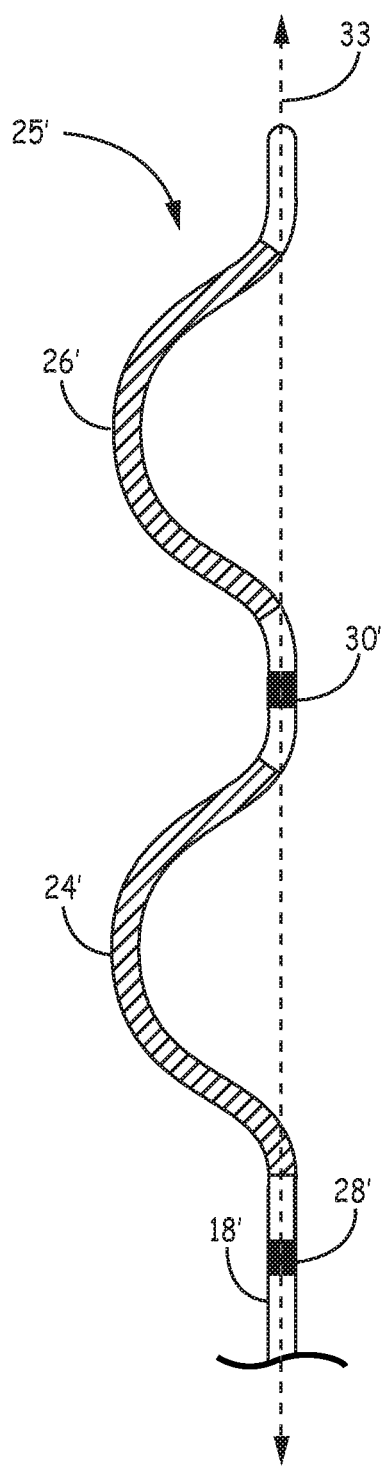
FIG. 3 is a conceptual diagram of a distal portion of an extra-cardiovascular lead having an electrode configuration according to another example.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε." Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in U.S. patent application Ser. No. 14/963,303, incorporated herein by reference in its entirety.

Figure 4:
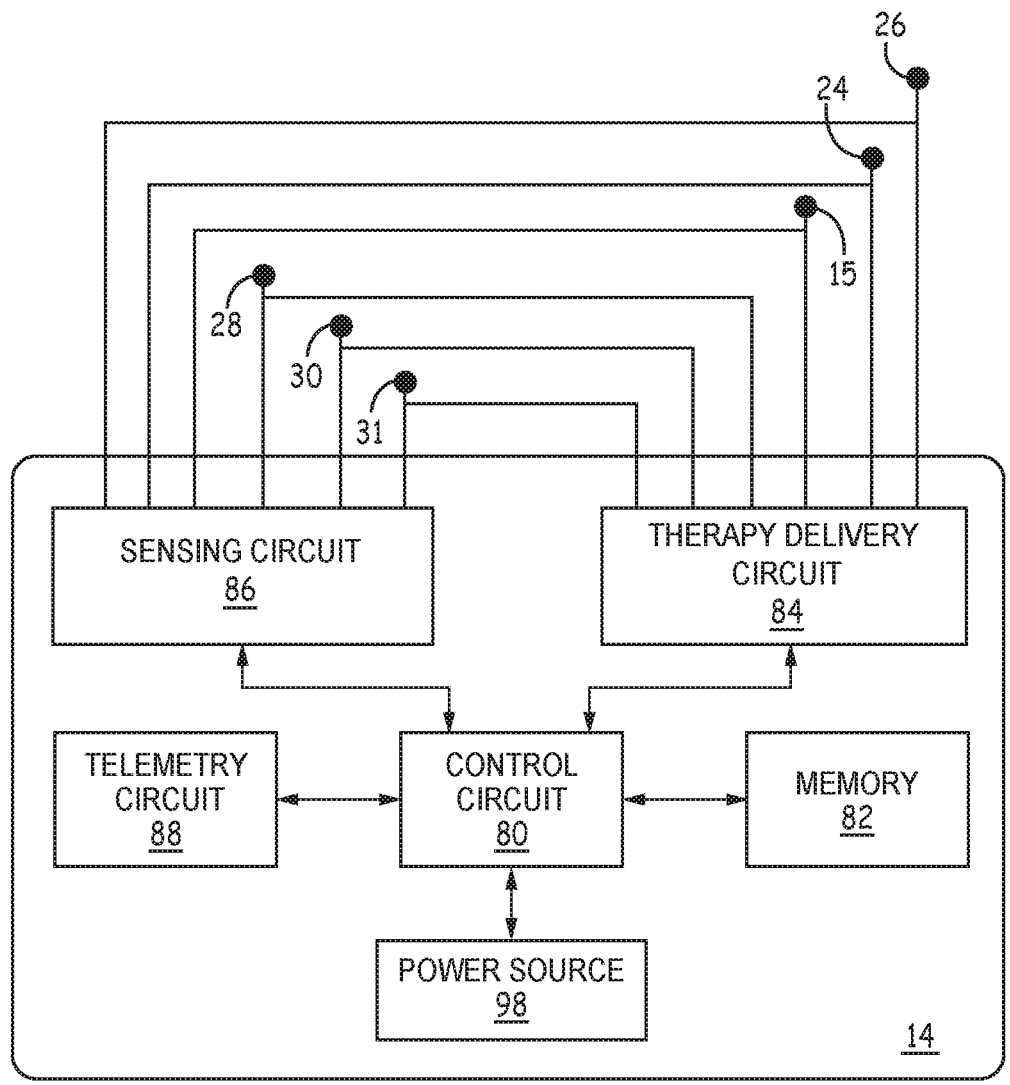
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor one or more cardiac electrical signals, determine when an electrical stimulation therapy is necessary, and deliver therapies as needed according to programmed therapy delivery algorithms and control parameters. The software, firmware and hardware are configured to detect and discriminate VT and VF for determining when ATP or CV/DF shocks are required and may determine when bradycardia pacing is needed. ICD 14 is coupled to an extra-cardiovascular lead, such as lead 16 carrying extra-cardiovascular electrodes 24, 26, 28, and 30 as show in FIGS. 3 and 31, if available, as shown in FIG. 1A, for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to a low voltage (LV) charging circuit and to a high voltage (HV) charging circuit included in therapy delivery circuit 84 for charging low voltage and high voltage capacitors, respectively, included in therapy delivery circuit 84 for producing respective low voltage pacing pulses, such as bradycardia pacing, post-shock pacing or ATP pulses, or for producing high voltage pulses, such as CV/DF shock pulses. In some examples, high voltage capacitors are charged and utilized for delivering pacing pulses instead of low voltage capacitors.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include one or more of an application specific integrated circuit (ASIC), an electronic circuit, a processor (shared, dedicated, or group) and memory that execute one or more software or firmware programs, a combinational logic circuit, state machine, or other suitable components or combination of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components is intended to highlight different functional aspects and does not necessarily imply that such components must be realized by separate hardware or software components. Rather, functionality associated with one or more components may be performed by separate hardware, firmware or software components, or integrated within common hardware, firmware or software components. For example, sensing operations may be performed by sensing circuit 86 under the control of control circuit 80 and may include operations implemented in a processor executing instructions stored in memory 82 and control signals such as timing and sensing threshold amplitude signals sent from control circuit 80 to sensing circuit 86.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, and 30 (and 31 if present as shown in FIGS. 1A and 2A) carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 is enabled to selectively monitor one or more sensing vectors at a time selected from the available electrodes 24, 26, 28, 30, 31 and housing 15. For example, sensing circuit 86 may include switching circuitry for selecting which of electrodes 24, 26, 28, 30, 31 and housing 15 are coupled to sense amplifiers or other cardiac event detection circuitry included in sensing circuit 86. Switching circuitry may include a switch array, switch matrix, multiplexer, or any other type of switching device suitable to selectively couple components of sensing circuit 86 to selected electrodes. In some instances, control circuit 80 may control the switching circuitry to selectively couple sensing circuit 86 to one or more sense electrode vectors. The cardiac event detection circuitry within sensing circuit 86 may include one or more sense amplifiers, filters, rectifiers, threshold detectors, comparators, analog-to-digital converters (ADCs), or other analog or digital components.

In some examples, sensing circuit 86 includes multiple sensing channels for acquiring cardiac electrical signals from multiple sensing vectors selected from electrodes 24, 26, 28, 30, 31 and housing 15. Each sensing channel may be configured to amplify, filter and rectify the cardiac electrical signal received from selected electrodes coupled to the respective sensing channel to improve the signal quality for sensing cardiac events, such as R-waves. For example, each sensing channel may include a pre-filter and amplifier for filtering and amplifying a signal received from a selected pair of electrodes. The resulting raw cardiac electrical signal may be passed from the pre-filter and amplifier to cardiac event detection circuitry for sensing cardiac events from the received cardiac electrical signal. Cardiac event detection circuitry may include a rectifier, post-filter and amplifier, a sense amplifier, comparator, and/or analog-to-digital converter for detecting a cardiac event when the cardiac electrical signal crosses a sensing threshold. The sensing threshold is automatically adjusted by sensing circuit 86 under the control of control circuit 80, based on timing intervals and sensing threshold values determined by control circuit 80, stored in memory 82, and/or controlled by hardware of control circuit 80 and/or sensing circuit 86. Some sensing threshold control parameters may be programmed by a user and passed from control circuit 80 to sensing circuit 86 via a data bus.

As described herein, sensing circuit 86 may sense R-waves according to a sensing threshold that is automatically adjusted to multiple threshold levels at specified times after a sensing threshold crossing. Multiple threshold levels and the time intervals over which each threshold level or value is applied may be used to provide accurate R-wave sensing while minimizing T-wave oversensing and P-wave oversensing. If T-waves and/or P-waves are falsely sensed as R-waves, due to a cardiac electrical signal crossing the R-wave sensing threshold, a tachyarrhythmia may be falsely detected potentially leading to an unnecessary cardiac electrical stimulation therapy, such as ATP or shock delivery. This situation is avoided using the multi-level sensing threshold techniques disclosed herein while still providing VT and VF detection with a high sensitivity. Oversensing may also cause ICD 14 to inhibit bradycardia pacing pulses when pacing is actually needed. By avoiding oversensing using the multi-level sensing threshold, inhibiting of bradycardia pacing pulses when pacing is actually needed is avoided.

Upon detecting a cardiac event based on a sensing threshold crossing, sensing circuit 86 may produce a sensed event signal, such as an R-wave sensed event signal, that is passed to control circuit 80. The sensed event signals are used by control circuit 80 for detecting cardiac rhythms and determining a need for therapy. Sensing circuit 86 may also pass a digitized electrocardiogram (ECG) signal to control circuit 80 for morphology analysis performed for detecting and discriminating heart rhythms. In some examples, analysis of the digitized cardiac electrical signal is performed for determining R-wave sensing threshold control parameters as described in conjunction with FIG. 11.

Signals from the selected sensing vector may be passed through a bandpass filter and amplifier, provided to a multiplexer and thereafter converted to multi-bit digital signals by an analog-to-digital converter, all included in sensing circuit 86, for storage in random access memory included in memory 82 under control of a direct memory access circuit via a data/address bus. Control circuit 80 may be a microprocessor based controller that employs digital signal analysis techniques to characterize the digitized signals stored in random access memory of memory 82 to recognize and classify the patient's heart rhythm employing any of numerous signal processing methodologies for analyzing cardiac signals and cardiac event waveforms, e.g., R-waves. Examples of algorithms that may be performed by ICD 14 for detecting, discriminating and treating tachyarrhythmia which may be adapted to utilize multi-sensing threshold techniques described herein for sensing cardiac electrical signals are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery circuit 84 includes charging circuitry, one or more charge storage devices, such as one or more high voltage capacitors and in some examples one or more low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when ATP or other cardiac pacing pulses are delivered.

For example, control circuit 80 may include pacer timing and control circuitry having programmable digital counters set by the microprocessor of the control circuit 80 for controlling the basic time intervals associated with various pacing modes or anti-tachycardia pacing sequences delivered by ICD 14. The microprocessor of control circuit 80 may also set the amplitude, pulse width, polarity or other characteristics of the cardiac pacing pulses, which may be based on programmed values stored in memory 82.

During pacing, escape interval counters within the pacer timing and control circuitry are reset upon sensing of R-waves as indicated by signals from sensing circuit 86. In accordance with the selected mode of pacing, pacing pulses are generated by a pulse output circuit of therapy delivery circuit 84. The pace output circuit is coupled to the desired electrodes via switch matrix for discharging one or more capacitors across the pacing load. The escape interval counters are reset upon generation of pacing pulses, and thereby control the basic timing of cardiac pacing functions. The durations of the escape intervals are determined by control circuit 80 via a data/address bus. The value of the count present in the escape interval counters when reset by sensed R-waves can be used to measure R-R intervals for detecting the occurrence of a variety of arrhythmias.

Memory 82 includes read-only memory (ROM) in which stored programs controlling the operation of the control circuit 80 reside. Memory 82 may further include random access memory (RAM) configured as a number of recirculating buffers capable of holding a series of measured intervals, counts or other data for analysis by the control circuit 80 for predicting or diagnosing an arrhythmia.

In response to the detection of VT, ATP therapy can be delivered by loading a regimen from the microprocessor included in control circuit 80 into the pacer timing and control circuit according to the type and rate of tachycardia detected. In the event that higher voltage cardioversion or defibrillation pulses are required, the control circuit microprocessor activates cardioversion and defibrillation control circuitry included in control circuit 80 to initiate charging of the high voltage capacitors of via a charging circuit, both included in therapy delivery circuit 84, under the control of a high voltage charging control line. The voltage on the high voltage capacitors is monitored via a voltage capacitor line, which is passed to control circuit 80. When the voltage reaches a predetermined value set by the microprocessor of control circuit 80, a logic signal is generated on a capacitor full line passed to therapy delivery circuit 84, terminating charging. The defibrillation or cardioversion pulse is delivered to the heart under the control of the pacer timing and control circuitry by an output circuit of therapy delivery circuit 84 via a control bus. The output circuit determines the electrodes used for delivering the cardioversion or defibrillation pulse and the pulse wave shape. Therapy delivery and control circuitry generally disclosed in any of the above-incorporated patents may be implemented in ICD 14.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 5:
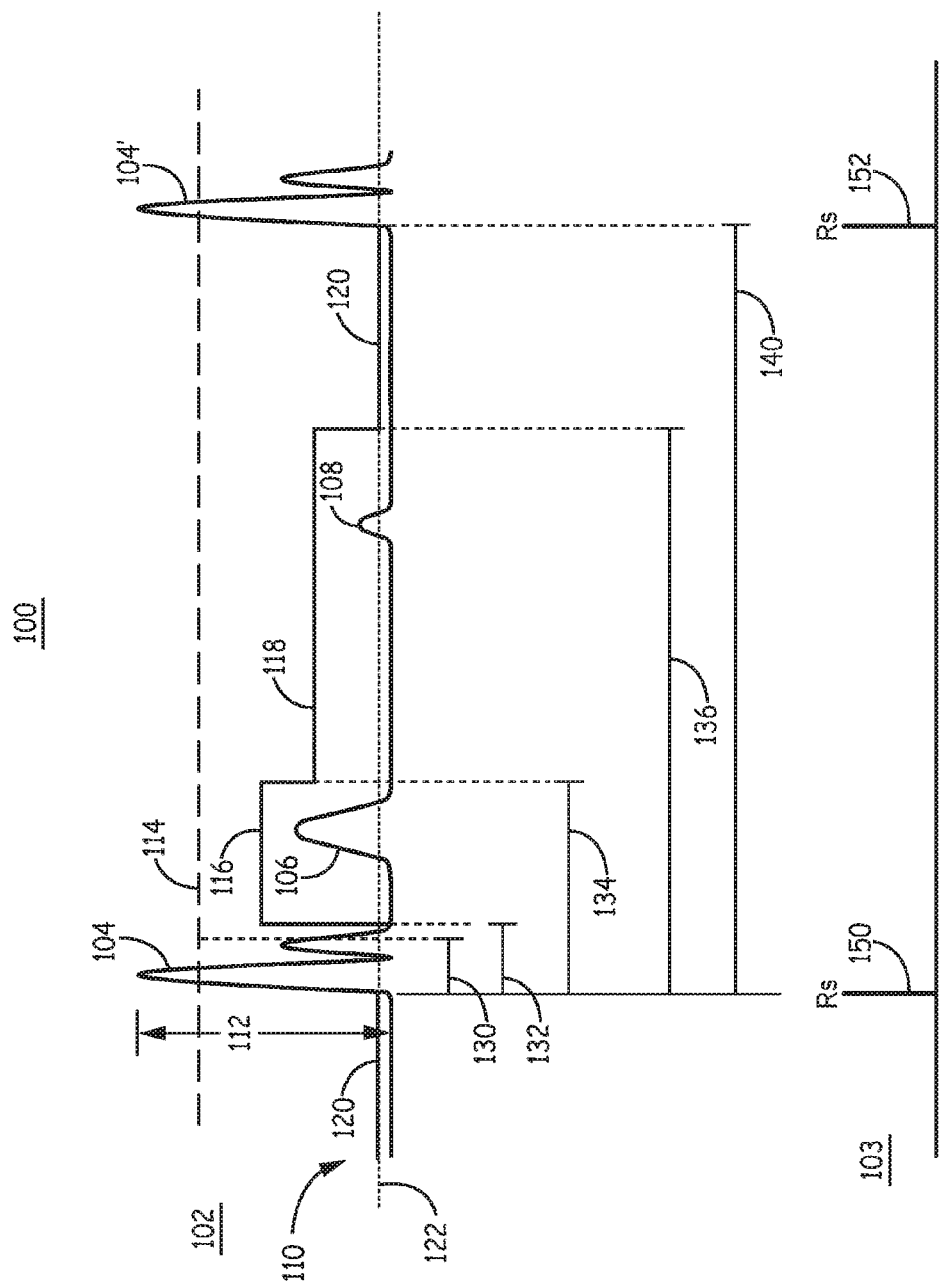
FIG. 5 is a timing diagram showing a filtered and rectified cardiac electrical signal and R-wave sensed event signals produced by a sensing circuit of the ICD of FIG. 4.

FIG. 5 is a timing diagram 100 showing a band-pass filtered and rectified cardiac electrical signal 102 and R-wave sensed event signals 103 produced by sensing circuit 86. The cardiac electrical signal 102 includes R-waves 104, 104', T-wave 106, and P-wave 108. As used herein, "R-wave sensing" generally refers to sensing the intrinsic QRS complex of a cardiac electrical signal for the purposes of detecting and discriminating intrinsic ventricular rhythms, e.g., for detecting and discriminating ventricular fibrillation, ventricular tachycardia, supraventricular tachycardia or other types of intrinsic heart rhythms. Sensing circuit 86 automatically adjusts an R-wave sensing threshold 110 to multiple threshold values 116, 118, and 120. The multiple threshold values 116, 118, and 120 may be determined by control circuit 80 based on the maximum peak amplitude 112 of a sensed R-wave 104 and passed to sensing circuit 86 along with multiple timing intervals 130, 132, 134 and 136 for controlling the R-wave sensing threshold 110 for detecting of the next R-wave 104'. Threshold values 116, 118 and 120 of R-wave sensing threshold 110 may also be referred to as threshold "levels" or "settings" or merely as "thresholds" but all refer to different voltage amplitudes which, when crossed by a positive-going, rectified band-pass filtered cardiac electrical signal, result in an R-wave sensed event signal being produced by sensing circuit 86.

In the example shown, R-wave 104 is sensed by sensing circuit 86 when the cardiac electrical signal 102 crosses R-wave sensing threshold 110, which is set to threshold value 120 at the time of the threshold crossing. An R-wave sense event signal 150 is generated. Upon sensing the R-wave 104, a blanking interval 130 may be started. The blanking interval may be a fixed time interval controlled by hardware that prevents the R-wave 104 from being sensed twice. The blanking interval 130 is 120 ms in one example, and may be 120 ms to 160 ms in other examples. During the blanking interval 130, a peak detector circuit included in sensing circuit 86 or control circuit 80 determines the maximum peak amplitude 112 of R-wave 104.

At the expiration of the blanking interval 130, the maximum peak amplitude 112 is used to determine the sensing threshold values 116 and 118. In one example, a second blanking interval 132 is started upon sensing R-wave 104 and is slightly longer than the first blanking interval 130. Upon expiration of the first blanking interval 130, a microprocessor within control circuit 80 may fetch the R-wave peak amplitude and determine the first, starting threshold value 116 prior to expiration of the second blanking interval 132. The R-wave sensing threshold 110 may be set to the starting threshold value 116 upon expiration of the second blanking interval 132.

The second blanking interval 132 may be at least 20 ms longer than the first blanking interval 130. For example, second blanking interval 132 may be 140 ms to 180 ms long in some examples. In some implementations, the first blanking interval 130 is a hardware controlled blanking interval, and the second blanking interval 132 is a digital blanking interval controlled by firmware or software stored in memory 82. The second blanking interval 132 may be a user-programmable value so that it may be tailored to the patient, e.g., based on the width of R-wave 104. The control circuit 80 may determine the first, starting threshold value 116 as a percentage of the R-wave peak amplitude 112 during the interval between the expiration of the first blanking interval 130 and the expiration of the second blanking interval 132. This interval difference between the first and second blanking intervals 130 and 132 may be minimized in some examples to enable firmware processing time to determine the first, starting threshold value 116 but enable R-wave sensing as early as possible after expiration of the first blanking interval 130.

By implementing the second blanking interval 132 and computation of the starting threshold value 116 in firmware stored in memory 82 and executed by a microprocessor of control circuit 80, the multi-level R-wave sensing threshold 110 disclosed herein may be implemented in many existing ICD systems that already include a hardware-implemented blanking interval without requiring hardware modifications. The longer second blanking interval 132 may be fixed or programmable to account for wider R-waves that typically appear in a cardiac signal obtained using extra-cardiovascular electrodes compared to the R-wave width in intracardiac electrogram signals. Furthermore, implementation of the second blanking interval 132 as a digital blanking interval allows R-wave sensing threshold control techniques disclosed herein to operate in conjunction with other algorithms or methods being executed by hardware or firmware of ICD 14 for heart rhythm detection without modification. For example, ICD 14 may be configured to execute T-wave oversensing rejection algorithms implemented in hardware or firmware configured to determine a differential filtered cardiac electrical signal as generally disclosed in U.S. Pat. No. 7,831,304 (Cao, et al.), incorporated herein by reference in its entirety. By setting the second blanking interval 132 as a digital blanking interval controlled by firmware, the R-wave sensing threshold 110 may be controlled without altering operations performed by a T-wave oversensing rejection algorithm operating concurrently, which may be implemented in hardware.

In other examples, the first blanking interval 130, peak detector for determining R-wave peak amplitude 112, and the second blanking interval 132 may all be implemented in hardware, all be implemented in firmware or a combination of both. In some examples, the second blanking interval 132 may be programmable such that the time of the onset of R-wave sensing at the expiration of the second blanking interval 132, after the expiration of the first blanking interval 130, may be selected by a user according to patient need. When peak detection and determination of the starting threshold value 116 are implemented in hardware, a single hardware implemented blanking interval 130 may be used without requiring a second blanking interval 132 for providing firmware processing time during which the starting threshold value 116 is determined.

The first sensing threshold value 116 may set to a percentage of the R-wave peak amplitude 112. For example, the first sensing threshold value 116 may be 50% of peak amplitude 112, and may be from 40% to 60% in other examples. The percentage of peak amplitude 112 used to determine the starting threshold value 116 is selected to promote a high likelihood that the threshold value 116 is greater than a maximum amplitude of T-wave 106. The percentage of peak amplitude 112 used to determine starting threshold value 116 may be selected based on a previous baseline T-wave amplitude measurement or T/R amplitude ratio. The starting threshold value 116 is held constant over a sense delay interval 134 in the example shown to maintain the R-wave sensing threshold 110 above a maximum T-wave amplitude until a time point near the end or after the T-wave 106. In other examples, the R-wave sensing threshold 110 may have a starting threshold value 116 that slowly decays over the sense delay interval 134. The decay rate, however, is selected to be relatively slow so that the ending threshold value at the expiration of the sense delay interval 134 is still greater than an expected T-wave amplitude.

Sense delay interval 134 may be started upon sensing R-wave 104, as shown in FIG. 5. Alternatively sense delay interval 134 may be started upon expiration of the second blanking interval 132. Sense delay interval 134 may be a user-programmable interval which may be tailored to patient need to encompass the T-wave 106, or at least the peak of the T-wave or a majority of the T-wave 106, to avoid T-wave oversensing. Sense delay interval 134 is 360 ms in one example and may be, with no limitation intended, 300 ms to 400 ms in other examples. By allowing a user to program the sense delay interval 134, the user has the ability to make adjustments to how early after a sensed R-wave the sensing threshold 110 is adjusted to a lower value, e.g., threshold value 118. In this way, if T-wave oversensing is being detected or reported by the ICD 14 or is being observed in cardiac electrical signal episodes that are stored by ICD 14 and transmitted to external device 40, the clinician has the ability to increase the sense delay interval 134 to avoid future T-wave oversensing without compromising detection of ventricular fibrillation or ventricular tachycardia.

Control circuit 80 may be configured to detect T-wave oversensing when it occurs and reject RR-intervals or other evidence of VT or VF when T-wave oversensing is detected. Examples of T-wave oversensing rejection algorithms that may be included in ICD 14 are generally disclosed in the above-incorporated '304 patent (Cao, et al.) and in U.S. Pat. No. 8,886,296 (Patel, et al.) and U.S. Pat. No. 8,914,106 (Charlton, et al.), also incorporated herein by reference in their entirety. In some examples, control circuit 80 may automatically increase the sense delay interval 134 and/or increase the starting value 116 of R-wave sensing threshold 110 in response to T-wave oversensing detection. Sense delay interval 134 may be increased up to a predefined maximum limit, e.g., 440 ms. If there is no TWOS detected for a predetermined time interval, for example one minute, one hour or one day, or if a tachyarrhythmia episode is being detected (e.g., three or more VT or VF intervals detected), sense delay interval 134 may be automatically reduced to a shorter interval or to a previous setting by control circuit 80.

In some examples, sense delay interval 134 is set equal to the tachycardia detection interval (TDI) used by control circuit 80 for detecting ventricular tachycardia (VT). Alternatively, sense delay interval 134 may be set slightly longer than the TDI, e.g., 10 to 20 ms longer than the TDI. Intervals between consecutively sensed R-waves, for example RR interval 140 between two consecutive R-wave sensed event signals 150 and 152 shown in FIG. 5, are compared to the TDI and to a fibrillation detection interval (FDI) by a cardiac rhythm analyzer included in control circuit 80. If an RR interval is less than the TDI, the cardiac rhythm analyzer may increase a VT interval counter. If the RR interval is less than the FDI, the cardiac rhythm analyzer may increase a VF interval counter. If the VT counter reaches a number of intervals to detect (NID) VT, VT is detected. If the VF counter reaches an NID to detect VF, VF is detected. By setting sense delay interval 134 to equal a programmed TDI, the R-wave sensing threshold 110 is kept high, at the starting threshold value 116, throughout the FDI and the TDI (which is longer than the FDI) such that the likelihood of a falsely sensed R-wave due to T-wave oversensing during the TDI is minimized, minimizing the likelihood an oversensed T-wave contributing to a VT or VF detection. If the T-wave 106 exceeds a lower value of R-wave sensing threshold 110 at an interval after the R-wave 104 that is longer than the TDI, the T-wave oversensed event will not contribute to VT detection. Accordingly, the sense delay interval 134 may be set to match the TDI programmed for VT detection and may be automatically adjusted to track the TDI if the TDI is reprogrammed to a different value.

Upon expiration of the sense delay interval 134, the sensing circuit 86 adjusts R-wave sensing threshold 110 to a second threshold value 118, lower than the starting value 116. The second threshold value 118 may be determined as a percentage of the R-wave peak amplitude 112. In one example, threshold value 118 is set to approximately 28% of the R-wave peak amplitude 112. Threshold value 118 may be set to 20% to 30% of the R-wave peak amplitude 112 in other examples. The second threshold value 118 is set to a value that is expected to be greater than the peak amplitude of the P-wave 108. P-waves are generally much lower in amplitude than R-waves, however, depending on the alignment of the sensing electrode vector relative to the cardiac axis and other factors, P-wave oversensing can occur in some patients, particularly when the lead 16 is positioned substernally as shown in FIG. 2A.

R-wave sensing threshold 110 is held at the second threshold value 118 until the expiration of a drop time interval 136. Drop time interval 136 may be started at the time R-wave 104 is sensed, as shown in FIG. 5, or upon expiration of blanking interval 130, blanking interval 132, or sense delay interval 134. When drop time interval 136 is started upon sensing R-wave 104, it may be set to 1.5 seconds or other relatively long interval to promote a high likelihood of maintaining the R-wave sensing threshold at the second value 118 until after P-wave 108, or at least until after the peak amplitude or majority of P-wave 108. Drop time interval 136 may be a fixed interval or may be programmable by the user. The drop time interval 136 may range from 0.8 to 2.0 seconds in other examples. In some examples, the drop time interval 136 may be adjusted with changes in heart rate. For example, as heart rate increases based on RR interval 140 measurements, the drop time interval 136 may be shortened. As heart rate decreases, the drop time interval 136 may be increased.

The second threshold value 118 is shown to be a constant value from the expiration of sense delay interval 134 until the expiration of drop time interval 136. In other examples, the second threshold value 188 may slowly decay until the expiration of drop time interval 136. The decay rate would be selected to be slow, however, so that the ending R-wave sensing threshold at the expiration of the drop time interval 136 is still expected to be greater than the P-wave amplitude to avoid P-wave oversensing. An example decay rate might be 10% of the maximum peak amplitude 112 per second.

If the cardiac electrical signal has not crossed R-wave sensing threshold 110 prior to expiration of the drop time interval 136, the R-wave sensing threshold 110 is adjusted from the second sensing threshold value 118 to a minimum sensing threshold value 120, which may be referred to as the "sensing floor." The R-wave sensing threshold 110 remains at the minimum sensing threshold 120 until the cardiac electrical signal 102 crosses the threshold 120. In the example shown, R-wave 104' is sensed when the minimum sensing threshold 120 is crossed, causing sensing circuit 86 to generate R-wave sense event signal 152.

In some examples, the minimum sensing threshold value 120 is set equal to the programmed sensitivity setting 122 which may be, for example, 0.07 millivolts (mV), 0.15 mV, 0.3 mV, 0.6 mV or higher. The programmed sensitivity setting 122 may establish the minimum possible sensing threshold value in some examples; in which case the R-wave sensing threshold 110 is never set below the programmed sensitivity setting 122. The sensitivity setting 122 may be programmable between 0.075 and 1.2 millivolts (mV) in one example and may be selected by a user as the minimum voltage threshold required to sense a cardiac event from cardiac signal 102. As the value of the sensitivity setting 122 decreases, sensitivity of the sensing circuit for sensing low amplitude signals increases. As such, a low sensitivity setting 122 corresponds to high sensitivity for sensing R-waves. The lowest setting, e.g., 0.07 mV, corresponds to the highest sensitivity, and the highest setting, e.g., 1.2 mV, corresponds to the lowest sensitivity of sensing circuit 86 for sensing R-waves.

Peaks of the cardiac electrical signal 102 that have a maximum voltage below the programmed sensitivity setting 122 are considered noise or events that are not intended to be sensed, which may include P-waves in some examples. When T-wave or P-wave sensing is detected or observed, the user may reprogram the sensitivity setting 122 to a higher setting (lower sensitivity). However, by providing the multi-threshold R-wave sensing threshold 110, controlled using a programmable sense delay time interval 134 and the drop time interval 136, the programmed sensitivity setting 122 may be kept at a low value to provide high sensitivity for sensing R-waves and low amplitude fibrillation waves while still minimizing the likelihood of T-wave and P-wave oversensing.

In addition to determining the starting threshold value 116 and the second threshold value 118, control circuit 80 may establish a maximum R-wave sensing threshold limit 114 that limits the maximum starting value of R-wave sensing threshold 110. In some cases, a maximum R-wave sensing threshold limit 114 is set as a fixed multiple or fixed gain of the programmed sensitivity setting 122, for example a gain of eight to ten times the sensitivity setting 122. In other examples, the gain applied to the programmed sensitivity setting 122 for establishing a maximum R-wave sensing threshold limit 114 is a variable gain. The variable gain may be defined to be dependent on the programmed sensitivity setting 122.

Figure 6:
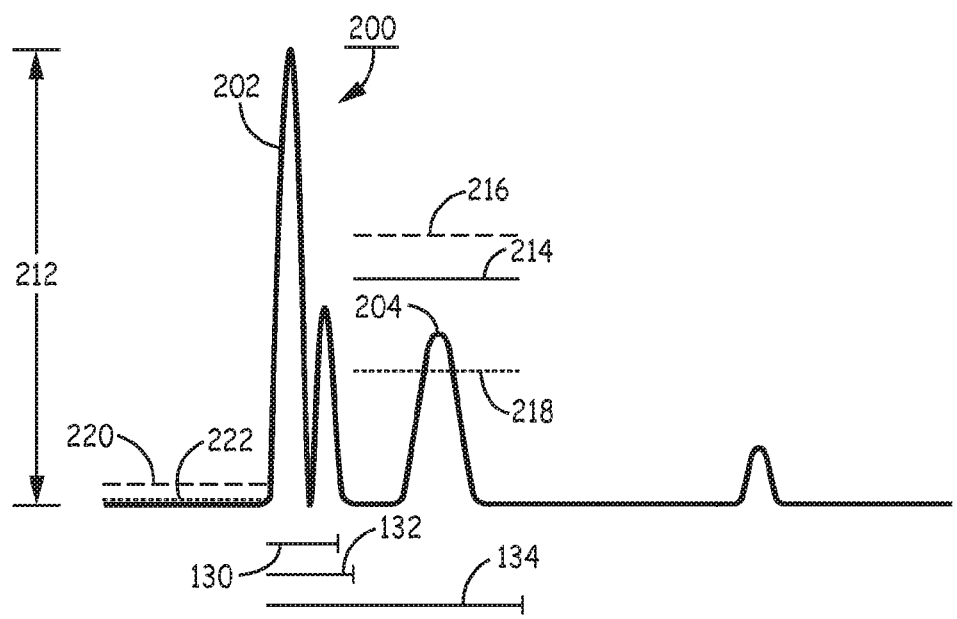
FIG. 6 is a diagram of a filtered and rectified cardiac electrical signal and a maximum sensing threshold limit according to one example.

FIG. 6 is a diagram of a filtered and rectified cardiac electrical signal 200 including R-wave 202 and T-wave 204. In this example, a maximum R-wave sensing threshold limit 216 or 218 is set as a fixed multiple of the programmed sensitivity setting 220 or 222, respectively. As can be seen in this example, in some cases, when large amplitude R-waves and T-waves occur, the maximum R-wave sensing threshold limit 218 set as a fixed multiple of the programmed sensitivity setting 222 may result in T-wave oversensing because T-wave 204 crosses the maximum R-wave sensing threshold limit 218. In this example, the maximum peak amplitude 212 of R-wave 202 is 10 mV, and the sensitivity setting 222 is programmed to 0.3 mV. The maximum R-wave sensing threshold limit 218 is set to 3 mV, when a fixed gain of 10 times the sensitivity setting is used to set the maximum threshold limit 218. In this situation of a very large R-wave 202, the first sensing threshold value 214 determined as a percentage (50% in the example shown) of the maximum peak amplitude 212 of the R-wave 202 is greater than the maximum sensing threshold limit 218. As such, the R-wave sensing threshold is set to the maximum sensing threshold limit 218 at the expiration of the second blanking interval 132 until the expiration of sense delay interval 134, which would result in T-wave oversensing since the maximum limit 218 is less than the amplitude of T-wave 204.

In order to prevent T-wave oversensing, a higher sensitivity setting 220 could be programmed, for example 0.6 mV. The maximum sensing threshold limit 216 is 6 mV in the example of the programmed sensitivity setting 220 being 0.6 mV and a fixed gain of 10 being used to determine the maximum limit 216. This maximum threshold limit 216 is greater than the starting sensing threshold value 214 determined as a percentage of R-wave amplitude peak 212, which is 50% of 10 mV or 5 mV in this example. This starting threshold value 214 is applied as the R-wave sensing threshold upon expiration of the second blanking interval 132 since it is less than the maximum threshold limit 216. The starting threshold value 214 does not result in T-wave oversensing because the amplitude of T-wave 204 is less than the starting sensing threshold value 214.

As can be seen by the illustrative example of FIG. 6, in the presence of large amplitude R-waves and T-waves, T-wave oversensing can occur when a maximum sensing threshold limit is determined as a fixed gain of the sensitivity setting and the sensitivity setting is low. In order to avoid T-wave oversensing, the sensitivity setting can be increased to lower the sensitivity, e.g., to 0.6 mV from 0.3 mV as represented by sensitivity setting 220 and sensitivity setting 222, respectively, in FIG. 6. The higher sensitivity setting, however, makes sensing circuit 86 less sensitive to low amplitude R-waves that may occur during VT or VF, potentially resulting in under-detection of ventricular tachyarrhythmia episodes.

Figure 7:
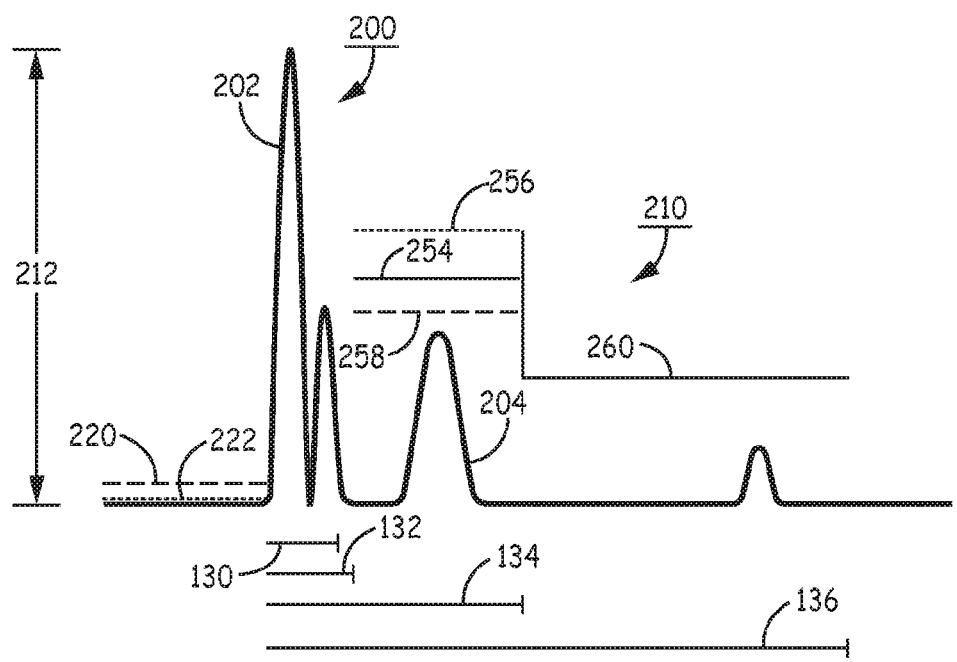
FIG. 7 is a diagram of the cardiac electrical signal shown in FIG. 6 and maximum sensing threshold limits determined based on a variable, sensitivity-dependent gain.

FIG. 7 is a diagram of the cardiac electrical signal 200 shown in FIG. 6 with maximum sensing threshold limits 256 and 258 determined based on a variable, sensitivity-dependent gain. The gain or multiple of the programmed sensitivity setting used by control circuit 80 to determine the maximum sensing threshold limit is a function of the programmed sensitivity setting in some examples. The maximum sensing threshold limit may be inversely related to the programmed sensitivity setting such that a higher gain corresponds to a lower programmed sensitivity setting. For instance, control circuit 80 may compute a variable gain for determining a maximum sensing threshold limit by determining an inverse proportion of the sensitivity setting and adding a constant using the equation G=A+B/S where A and B are constants and S is the programmed sensitivity (B/S being an inverse proportion of the programmed sensitivity setting). In some examples, the gain determined for each available programmable sensitivity setting is stored in a look-up table in memory 80 and is retrieved by control circuit 80 each time a new sensitivity setting is programmed.

In one example, A is at least 5 and B is at least 2. For instance, A may be equal to 6 and B may be equal to 2.5 in the equation given for the gain G above. The minimum possible value of the maximum sensing threshold limit will approach 2.5 since the maximum sensing threshold limit is the product of the gain and the programmed sensitivity setting, or 6 S+2.5 where S equals the programmed sensitivity setting. For a programmable range of sensitivity settings from 0.075 mV to 1.2 mV, the sensitivity-dependent gain ranges from approximately 39.3 for the lowest sensitivity setting of 0.075 mV (corresponding to highest sensitivity) to approximately 8.1 for the highest sensitivity setting of 1.2 mV (corresponding to the lowest sensitivity). The higher the sensitivity, i.e., the lower the sensitivity setting, the higher the sensitivity-dependent gain is. For a programmed sensitivity of 0.3 mV, G=6+2.5/0.3 or approximately 14.3 in this example. The maximum sensing threshold limit 258 determined when the sensitivity setting 222 is programmed to 0.3 mV is the gain, 14.3, multiplied by the sensitivity setting, 0.3 mV, or approximately 4.3 mV. This maximum sensing threshold limit 258 is less than the first sensing threshold value 254 determined as a percentage (50% in this example) of R-wave peak amplitude 212. As a result, the R-wave sensing threshold 210 will be set to the maximum sensing threshold limit 258, but in this case the sensing threshold limit 258 set using the variable gain is greater than the amplitude of T-wave 204, thereby avoiding T-wave oversensing while still allowing a high sensitivity (low sensitivity setting) to be used for sensing low amplitude waveforms during VT or VF (especially spontaneous fine VF).

Continuing with the illustrative example given above, the maximum sensing threshold limit 256 determined for a programmed sensitivity setting of 0.6 mV 220 is determined using a sensitivity-dependent gain of approximately 10.2 (G=6+2.5/0.6). The maximum sensing threshold limit 256 is 6.1 mV in this case (0.6 mV multiplied by the gain of 10.2), which is greater than the starting sensing threshold value 254 determined as a percentage (e.g., 50%) of the R-wave peak amplitude 212. In this case, the R-wave sensing threshold 210 is set to the starting sensing threshold value 254 at the expiration of the second blanking period 132 (shown in FIG. 5).

In both cases of 0.6 mV sensitivity setting 220 and 0.3 mV sensitivity setting 222, the R-wave sensing threshold value during the sense delay interval 134 avoids T-wave oversensing in the presence of large amplitude R-waves and T-waves. Even when a low sensitivity setting is used, e.g., 0.3 mV or less, so that sensing circuit 86 remains highly sensitive to small R-waves that may occur during a ventricular tachyarrhythmia, T-wave oversensing is avoided by using a sensitivity-dependent variable gain for determining the maximum R-wave sensing threshold limit.

At the expiration of the sense delay interval 134, the R-wave sensing threshold is adjusted from the starting threshold 254 or 258, to the second threshold 260 which is determined as 25% of the R-wave peak amplitude 212 in this example. The second threshold 260 remains in effect until the drop time interval 136 expires (described in FIG. 5) after which the R-wave sensing threshold 210 drops to the programmed sensitivity setting, either the 0.6 mV sensitivity setting 220 or the 0.3 mV sensitivity setting 222 in the example shown in FIG. 7.

Figure 8A:
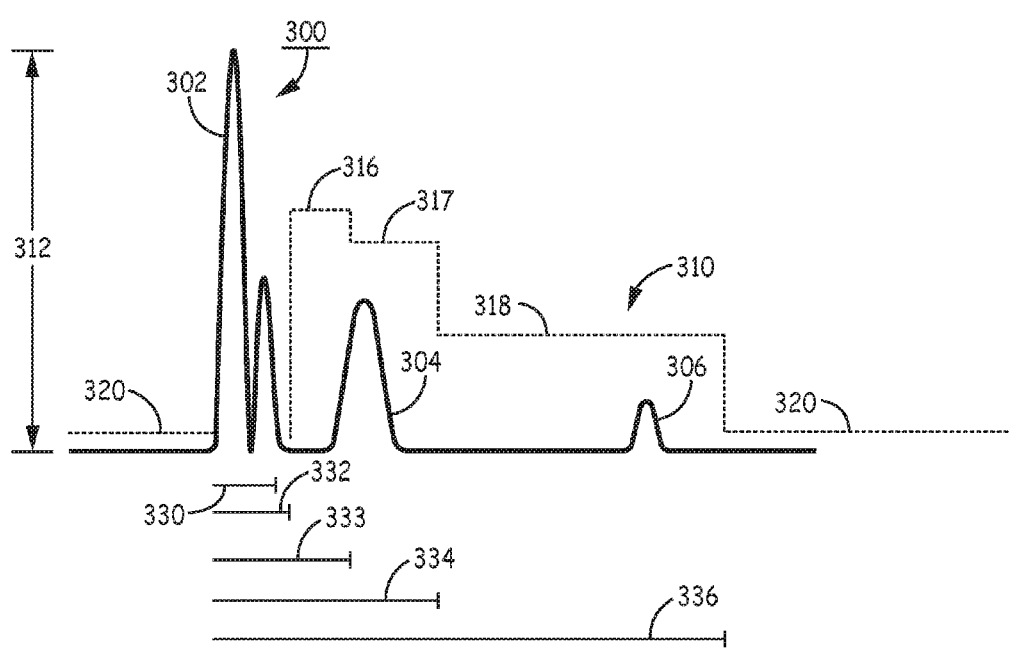
FIG. 8A is a diagram of a multi-level R-wave sensing threshold according to another example.

FIG. 8A is a diagram of a filtered and rectified cardiac electrical signal 300 including an R-wave 302, a T-wave 304, and a P-wave 306 and an automatically adjusted R-wave sensing threshold 310 having multiple sensing threshold values 316, 317 and 318. In the examples of FIGS. 5, 6 and 7, the R-wave sensing threshold 310 is set to the first, starting threshold value and second threshold value before dropping to the programmed sensitivity setting. In other examples, the R-wave sensing threshold 310 may be adjusted to three or more threshold values before dropping to the programmed sensitivity setting.

As shown in FIG. 8A, the starting threshold value 316 may be determined as a first percentage of the R-wave peak amplitude 312 determined during first blanking interval 330, e.g., 62.5% or between 55% and 70% of the peak R-wave amplitude 312. The starting threshold value 316 may be maintained from the expiration of the second blanking interval 332 until the expiration of a first sense delay interval 333. The first sense delay interval 333 may be approximately 180 ms, for example 30 to 60 ms longer than the second blanking interval 332. The higher starting threshold value 316 applied for a short interval may reduce the likelihood of double sensing the R-wave 302, particularly in patients exhibiting a wide QRS complex.

Upon expiration of the first sense delay interval 333, the R-wave sensing threshold 310 is adjusted to a lower, second sensing threshold value 317, which may be between 30% and 60% of the R-wave peak amplitude 312, such as 50% of the R-wave peak amplitude 312. The second sensing threshold value 317 is maintained until expiration of the second sense delay interval 334, which may be between 300 and 360 ms, and may be set equal to a programmed TDI as described previously in conjunction with FIG. 5.

Upon expiration of the second sense delay interval 334, the third sensing threshold value 318 is applied until a drop time interval 336 expires, and the R-wave sensing threshold 310 falls to a minimum sensing threshold value 320, which may be equal to the programmed sensitivity setting. The third sensing threshold value 318 may be approximately 28% of the R-wave peak amplitude 312, or between 20% and 30% in other examples, and extend for a drop time interval 336 of one to two seconds, e.g., 1.5 seconds.

Figure 8B:
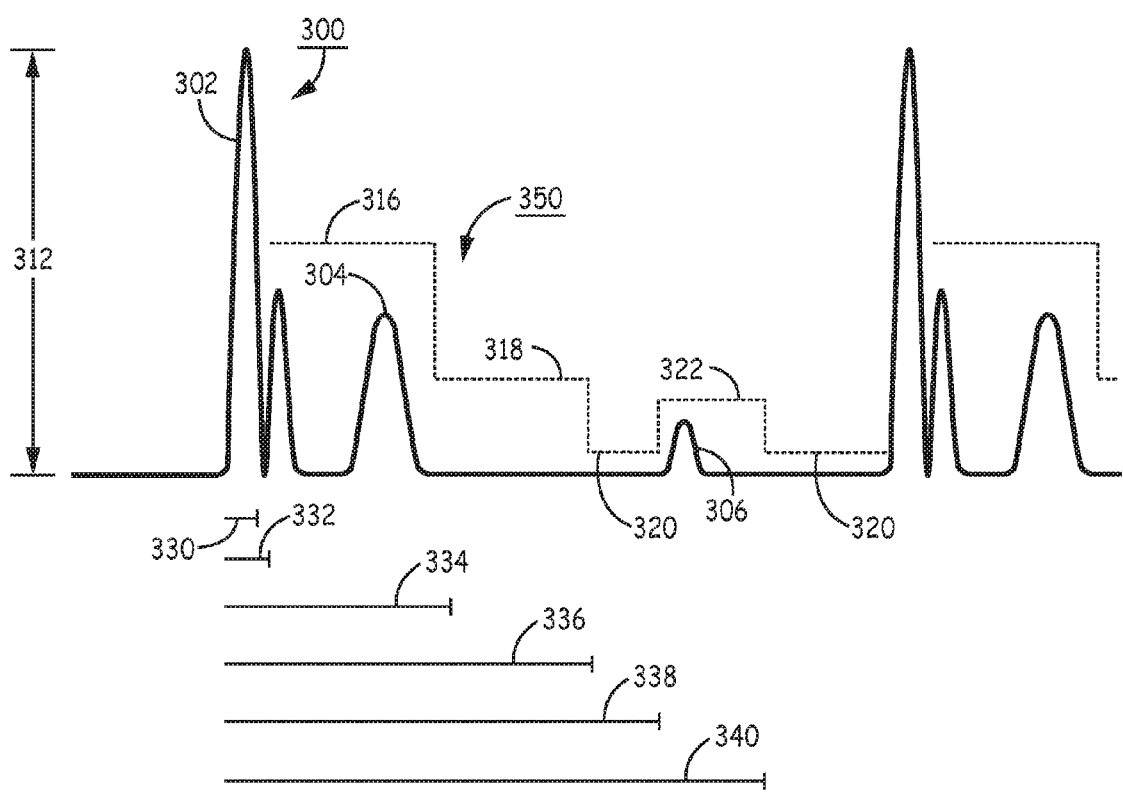
FIG. 8B is a diagram of a non-monotonic, multi-level R-wave sensing threshold according to another example.

FIG. 8B is a diagram of a non-monotonic, multi-level R-wave sensing threshold 350 according to another example. In the examples of FIGS. 5 and 8A, R-wave sensing threshold 110 and R-wave sensing threshold 310, respectively, are monotonically decreasing sensing thresholds. In other examples, the multi-level R-wave sensing threshold controlled by control circuit 80 is non-monotonic, including one or more step increases in R-wave sensing threshold value in addition to the decreasing step changes in sensing threshold value.

The filtered and rectified cardiac electrical signal 300, including R-wave 302, T-wave 304, and P-wave 306, and an automatically adjusted R-wave sensing threshold 350 are shown in FIG. 8B. R-wave sensing threshold 350 may include a starting sensing threshold value 316 beginning upon expiration of second blanking interval 332 and a second sensing threshold value 318 beginning after expiration of the sense delay interval 334. R-wave sensing threshold 350 drops to the programmed sensitivity setting 320 upon expiration of drop time interval 336.

If cardiac signal 300 does not cross the R-wave sensing threshold 350 before a maximum sensitivity interval 338 expires, the R-wave sensing threshold 350 is increased to a third sensing threshold value 322. The third sensing threshold value may be equal to the second sensing threshold value 318 or set as a percentage of a previously determined baseline P-wave maximum peak amplitude, e.g., 1.5 times a previously determined P-wave maximum peak amplitude. The maximum sensitivity interval 338 controls how long the R-wave sensitivity threshold 350 is held at the maximum sensitivity, i.e., the programmed sensitivity setting 320, before being increased to the third sensing threshold value 322. In some examples, the maximum sensitivity interval 338 is approximately 200 ms longer than the drop time interval 336 so that the R-wave sensing threshold 350 is set to the programmed sensitivity setting 320 for up to 200 ms if an R-wave sensing threshold crossing does not occur.

Upon expiration of the maximum sensitivity interval 338, R-wave sensing threshold 350 is increased to the third sensing threshold value 322 to minimize the likelihood of oversensing the P-wave 306 during very slow heart rates, when the P-wave 306 has an amplitude greater than the programmed sensitivity setting 320. By allowing the R-wave sensing threshold 350 to drop to the programmed sensitivity setting 320, to provide high sensitivity for up to a predefined time interval as controlled by interval 338, undersensing of low amplitude, fine VF waveforms is avoided. Sensing circuit 86 may sense low amplitude ventricular tachyarrhythmia waveforms after expiration of drop time interval 336 and before expiration of maximum sensitivity interval 338. If the heart rate is very slow, however, such that the P-wave 306 arrives relatively late after R-wave 302 and after expiration of drop-time interval 336, P-wave oversensing may be avoided by increasing the R-wave sensing threshold 350 to the third threshold value 322 while still providing an interval of high sensitivity to low amplitude tachyarrhythmia waveforms. The third sensing threshold value 322 may be maintained until a sensing threshold crossing occurs. In other examples, as shown in FIG. 8B, the third sensing threshold value 322 is held until a second drop time interval 340 expires, at which time the sensing threshold 350 is adjusted back to the programmed sensitivity setting 320.

Figure 9:
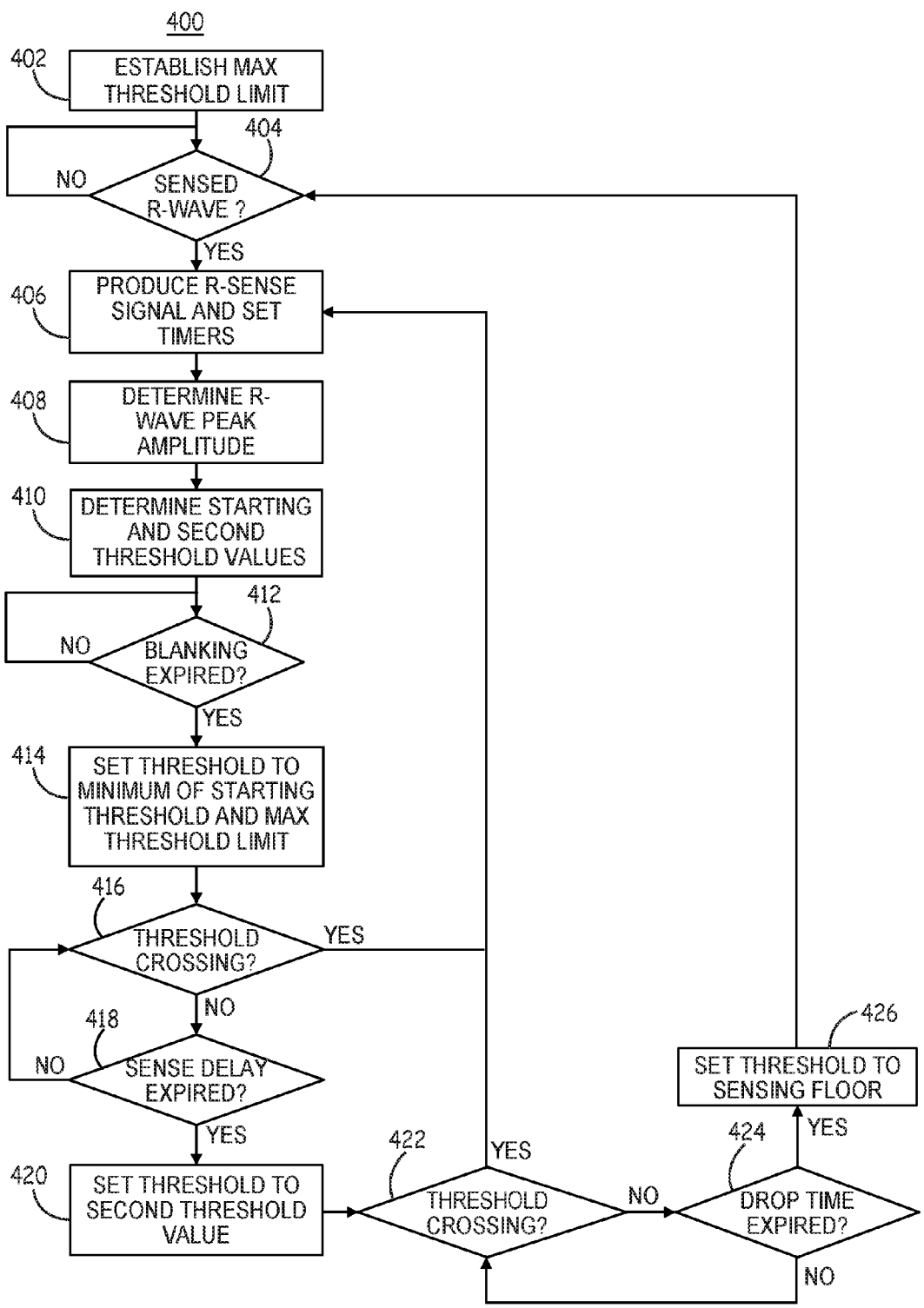
FIG. 9 is a flow chart of a method performed by the ICD of FIGS. 1A-2C for controlling the R-wave sensing threshold according to one example.

FIG. 9 is a flow chart 400 of a method for controlling the R-wave sensing threshold according to one example. At block 402, the control circuit 80 establishes the maximum threshold limit. The maximum threshold limit may be set based on a sensitivity-dependent gain as described in conjunction with FIG. 7. Control circuit 80 determines the sensitivity-dependent gain then computes the maximum threshold limit as the product of the gain and the programmed sensitivity setting. Alternatively, the maximum threshold limit may be set as a fixed multiple of the programmed sensitivity setting, as described in conjunction with FIG. 6. The maximum threshold limit is re-established at block 402 each time the sensitivity is reprogrammed to a different sensitivity setting.

At block 404, an R-wave is sensed in response to the cardiac electrical signal crossing the R-wave sensing threshold, which may initially be set to the maximum sensing threshold, a nominal sensing threshold, the programmed sensitivity setting or other starting value. In response to sensing an R-wave, sensing circuit 86 produces an R-wave sensed event signal at block 408, and control circuit 80 sets various timers or counters as described in conjunction with FIGS. 5 and 8A and 8B for controlling the multi-threshold R-wave sensing threshold. For example, a first blanking interval, which may be a hardware controlled blanking interval, a second blanking interval, which may be a digital blanking interval controlled by firmware stored in memory 82, a sense delay interval, a drop time interval, and a maximum sensitivity interval may be started upon sensing an R-wave due to a positive-going R-wave sensing threshold crossing of the cardiac electrical signal received by sensing circuit 86.

At block 408, the maximum peak amplitude of the sensed R-wave is determined. The R-wave peak amplitude may be determined by a peak track and hold circuit or other hardware or firmware. The R-wave peak amplitude is fetched by control circuit 80 at the expiration of the first blanking interval. Control circuit 80 determines the starting and second threshold values at block 410 as two different percentages of the R-wave peak amplitude. For example, the starting threshold value may be determined as 40 to 60% of the R-wave peak amplitude and the second threshold value may be determined as 20 to 30% of the R-wave peak amplitude. Control circuit 80 may execute firmware after expiration of the first blanking interval for determining these starting, first threshold value and second threshold value before expiration of the second blanking interval. The staring and second threshold values may be passed to sensing circuit 86 as control values used by circuitry of sensing circuit 86 for controlling the R-wave sensing threshold. In other examples, three or more threshold values are determined as described in conjunction with FIGS. 8A and 8B.

Upon expiration of the second blanking interval, as determined at block 412, the sensing circuit 86 sets the starting R-wave sensing threshold (block 414) to the starting threshold value determined as a percentage of the R-wave peak amplitude or to the maximum threshold limit, whichever is less, under the control of control circuit 80. If the cardiac electrical signal crosses the starting R-wave sensing threshold, as determined at block 416, the process returns to block 406 where sensing circuit 86 produces another R-wave sensed event signal and restarts the various control time intervals as described above.

If the sense delay interval expires at block 418 before the cardiac electrical signal crosses the R-wave sensing threshold, sensing circuit 86 adjusts the R-wave sensing threshold at block 420 to the second threshold value received from control circuit 80. If the cardiac electrical signal crosses the R-wave sensing threshold adjusted to the second threshold value, as determined at block 422, the process returns to block 406 to generate an R-wave sensed event signal and reset the control time intervals as described above. If the drop time interval expires at block 424 without the cardiac electrical signal crossing the R-wave sensing threshold (block 422), the sensing circuit 86 adjusts the R-wave sensing threshold to the minimum threshold value or sensing floor, which may be the programmed sensitivity setting, at block 426. Sensing circuit 86 waits for the cardiac electrical signal to cross the sensing floor at block 404 and the process repeats. In other examples, more than two drop steps in the sensing threshold value may be implemented, as described in FIG. 8A, and/or a step increase in the sensing threshold value may be included as described in FIG. 8B.

While not shown in FIG. 9, it is recognized that if a pacing therapy is enabled and a pacing pulse is delivered during the sense delay interval (e.g., an ATP pulse) or the drop time interval (e.g., a bradycardia or asystole back up pacing pulse) or any time prior to an R-wave sensing threshold crossing, the various timers used to control the R-wave sensing threshold may be reset and a previous starting R-wave sensing threshold value or a starting threshold value based on an average daily R-wave amplitude may be started following a post-pace blanking interval, which may be a longer blanking interval than the blanking interval used during intrinsic R-wave sensing. As such, the various timing intervals and threshold values shown in any of FIGS. 5-8B may be determined and applied for controlling the R-wave sensing threshold following a delivered pacing pulse and are not limited to being used following only intrinsic R-wave sensed events.

Furthermore, while the techniques have been described for controlling an R-wave sensing threshold for sensing R-waves attendant to ventricular depolarization, it is to be understood that aspects of the disclosed techniques may be used for controlling a cardiac event sensing threshold for sensing other cardiac signals, such as P-waves attendant to atrial depolarization or T-waves attendant to ventricular repolarization. For example, a maximum P-wave sensing threshold limit may be set based on a sensitivity-dependent gain and a programmed sensitivity; a maximum T-wave sensing threshold limit may be set based on a sensitivity-dependent gain and programmed sensitivity. P-wave and/or T-wave sensing thresholds may be controlled using multiple threshold levels and multiple time intervals.

Figure 10:
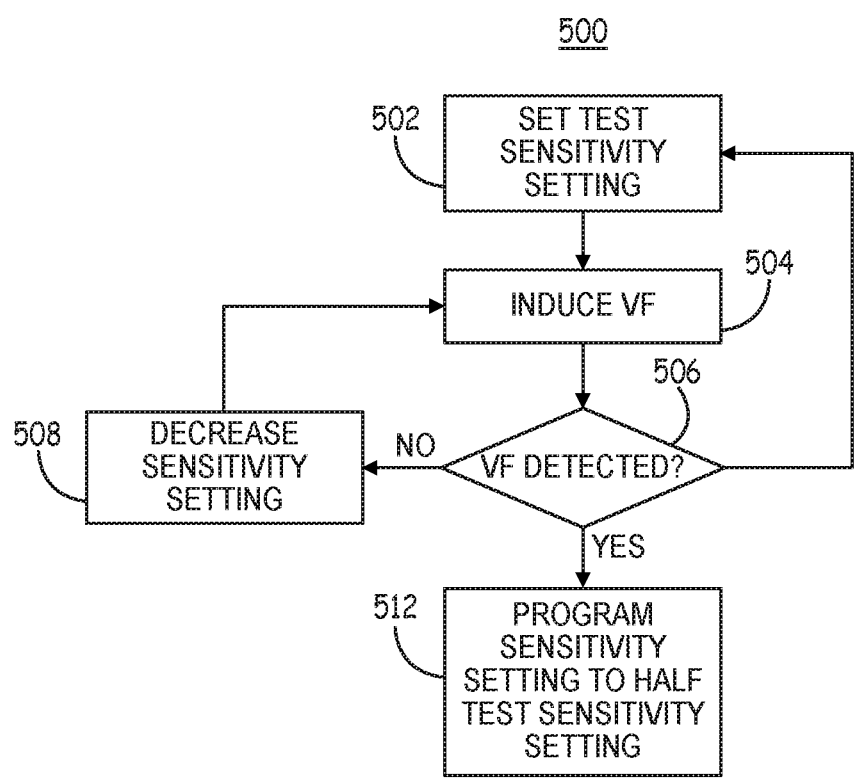
FIG. 10 is a flow chart of a method for selecting a sensitivity setting in the ICD system of FIGS. 1A-2C according to one example.

FIG. 10 is a flow chart of a method for selecting a sensitivity setting in ICD 14. The process shown in FIG. 10 may be performed at the time of ICD 14 implant or during a lead replacement procedure to determine a reliable sensitivity setting for detecting low amplitude fibrillation waves during VF. The process shown by flow chart 500 may be a semi-automated process executed by ICD 14 in response to programming commands received from external device 40.

At block 502, a test sensitivity setting is selected. The test sensitivity setting may be programmed by a user using external device 40 or may be a value two times a nominal sensitivity setting or a preferred sensitivity setting, which may be based on a measured R-wave amplitude. For example, if the R-wave amplitude observed on an electrocardiogram signal produced by ICD 14 and transmitted to external device 40 is at least 3 mV, a test sensitivity setting of 0.6 mV may be set at block 502 for a preferred sensitivity setting of 0.3 mV, half of the test setting.

At block 504, a user transmits a VF induction command to ICD 14 using external device 40. ICD 14 may induce VF using any implemented induction method, such as a T-shock, which is a large energy electrical pulse delivered during the vulnerable period associated with the T-wave. If VF is detected at the programmed sensitivity setting, "Yes" branch of block 506, a defibrillation shock is delivered according to programmed shock therapy control parameters to terminate the VF. If VF is not detected at the programmed sensitivity within a predetermined time limit, a shock is delivered to terminate the induced VF, and the sensitivity setting may be decreased, to increase the sensitivity to VF waveforms, at block 508 and VF is induced again. This process may be repeated one or more times as needed to determine the highest sensitivity setting that allow detection of VF. Alternatively, if VF is not detected at block 506 using the first sensitivity setting, a recording of the cardiac electrical signal during the induced VF may be used to determine the voltage amplitude of the VF waveforms and the sensitivity setting may be programmed lower than the VF waveform amplitude at block 512. In still other examples, if sensing circuit 86 includes two sensing channels, the cardiac electrical signal may be sensed using two different test sensitivity settings simultaneously to determine if one or both result in VF detection.

When VF is detected at the current test sensitivity setting, the sensitivity setting is programmed to one-half to one-third the test sensitivity setting. For example, if the sensitivity setting tested is 0.6 mV, the sensitivity setting is programmed to 0.3 mV at block 512. By using a sensitivity-dependent gain for setting the maximum R-wave sensing threshold limit, a lower sensitivity setting may be tested and used with confidence in avoiding T-wave and P-wave oversensing while still providing high sensitivity for detecting VF, both acutely and chronically after implantation of the ICD system 10. The R-wave amplitude of the cardiac electrical signal received by the extra-cardiovascular electrodes is similar during the acute phase (days or weeks) after implantation and after chronic implantation (months or years). Accordingly, the recommended sensitivity setting determined at block 512 need not change based on time since implant, unlike transvenous ICD systems which may have larger R-wave amplitude acutely and smaller R-wave amplitude chronically. A two-fold or three fold sensitivity safety margin may be used in the extra-cardiovascular ICD system 10 rather than higher safety margins which have been practiced in the past for transvenous ICD systems, such as a four-fold safety margin. Control of the R-wave sensing threshold as disclosed herein using a two- to three-fold sensitivity safety margin minimizes the risk of undersensing spontaneous fine VF (usually with small waveform amplitudes) while avoiding T-wave and P-wave oversensing.

Figure 11:
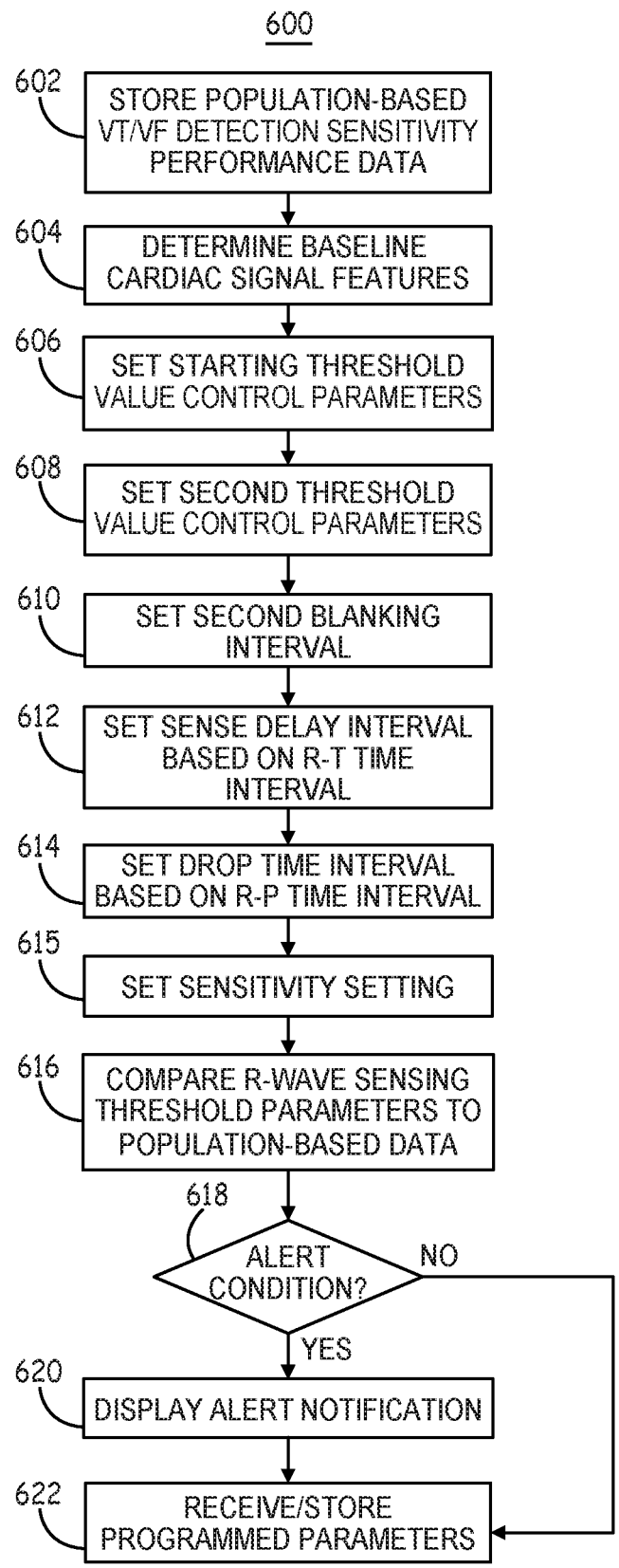
FIG. 11 is a flow chart of a method for selecting R-wave sensing threshold control parameters according to one example.

FIG. 11 is a flow chart 600 of a method for selecting R-wave sensing threshold control parameters according to one example. As described above in conjunction with FIG. 10, the sensitivity setting, which may define the minimum R-wave sensing threshold value, may be based at least in part on VF detection testing. The starting value of the R-wave sensing threshold may be set on a beat-by-beat basis based on the peak R-wave amplitude (as shown in FIG. 5). The gain applied to the sensitivity for setting the maximum R-wave sensing threshold value may be a variable gain that is dependent on the programmed sensitivity setting as described in conjunction with FIG. 7. In addition to these R-wave sensing threshold control parameters, other R-wave sensing threshold control parameters may be variable and/or programmable based on cardiac signal features determined for an individual patient to tailor optimal R-wave sensing threshold control for that patient and/or based on empirical data from a population of patients.

For example, the percentage of the R-wave peak amplitude used to set the starting threshold value 116, the second blanking interval 132, the sense delay interval 134, the second, lower threshold value 118, and the drop time interval 136 (all shown in FIG. 5) may all be programmable or variable values that may be tailored to an individual patient and/or based on sensitivity performance data obtained from a population of patients. Other control parameters such as a second sensing delay interval 334 as shown in FIG. 8A or a maximum sensitivity interval 338 as shown in FIG. 8B may also be programmable and tailored individually to a patient.

At block 602, population-based VT/VF detection sensitivity for one or more individual R-wave sensing threshold control parameter settings and/or combinations of R-wave sensing threshold control parameter settings may be stored in ICD memory 82 and/or in memory 53 of external device 40. For example, a VT/VF detection sensitivity curve as a function of the programmed sensitivity setting 122, second blanking interval 132, drop time interval 136, or other R-wave sensing control parameters described above may be determined from empirical data gathered from a population of ICD patients.

Figure 12:
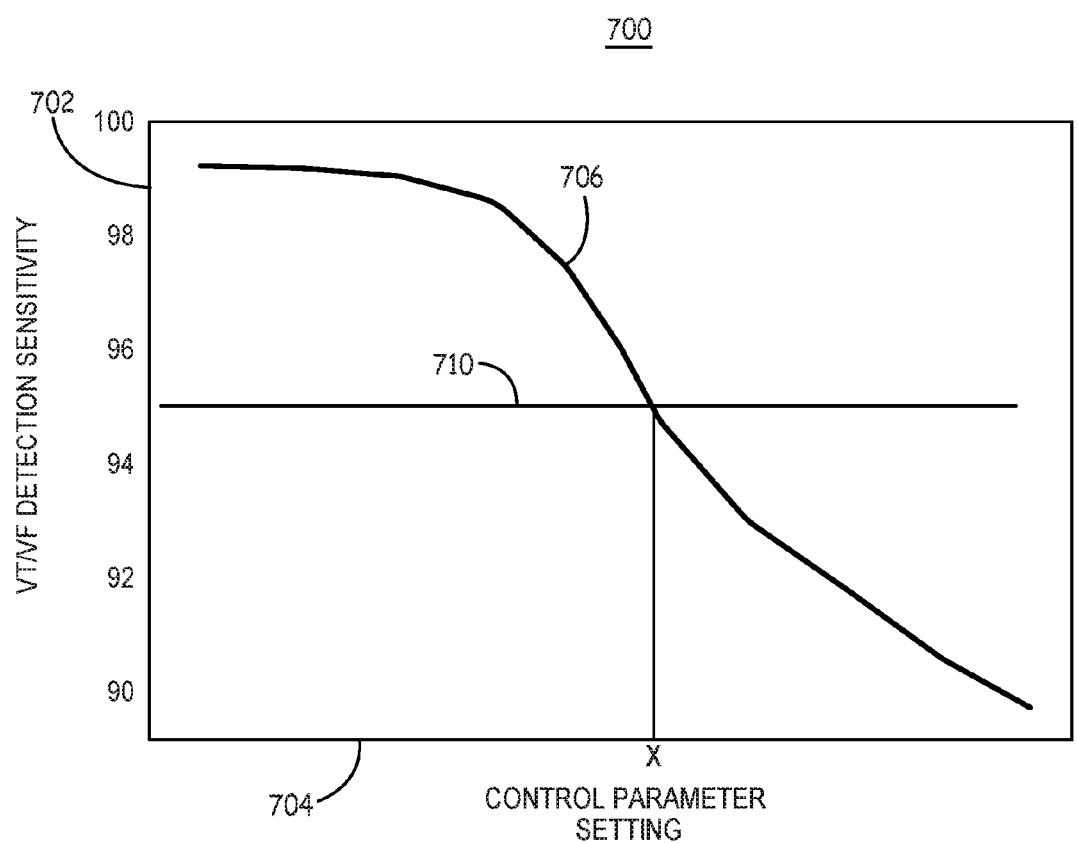
FIG. 12 is a plot of an example of a ventricular tachycardia/ventricular fibrillation (VT/VF) detection sensitivity curve.

A plot 700 of an illustrative VT/VF detection sensitivity curve 706 is depicted in FIG. 12. VT/VF detection sensitivity, expressed as the percentage of all VT/VF episodes actually detected, is plotted along the y-axis 702 as a function of an R-wave sensing threshold control parameter setting plotted along the x-axis 704. The sensing control parameter is indicated generically in FIG. 12 but may be the second blanking interval 132, the percentage used to determining the starting value 116 of the R-wave sensing threshold, the sense delay interval 134, the percentage used to determine the second value 118 of the R-wave sensing threshold, the drop time interval 136, the sensitivity setting 122 (all shown in FIG. 5) or any of the other R-wave sensing threshold control parameters described herein.

An alert threshold 710 may be set, below which the VT/VF detection sensitivity falls below VT/VF detection performance expectations, e.g., 95%. When the control parameter setting has a programmed value greater than "X", the VT/VF detection sensitivity falls below the alert threshold 710. As described below, stored VT/VF detection sensitivity data may be used by control circuit 80 (or external device processor 52) to look up an expected VT/VF detection sensitivity for a programmed R-wave sensing threshold control parameter individually or in combination with other parameter values in a multi-parameter n-dimensional model of detection sensitivity. If the detection sensitivity falls below an alert threshold 710 for ICD performance expectations, a clinician alert may be generated as described below.

Figure 13:
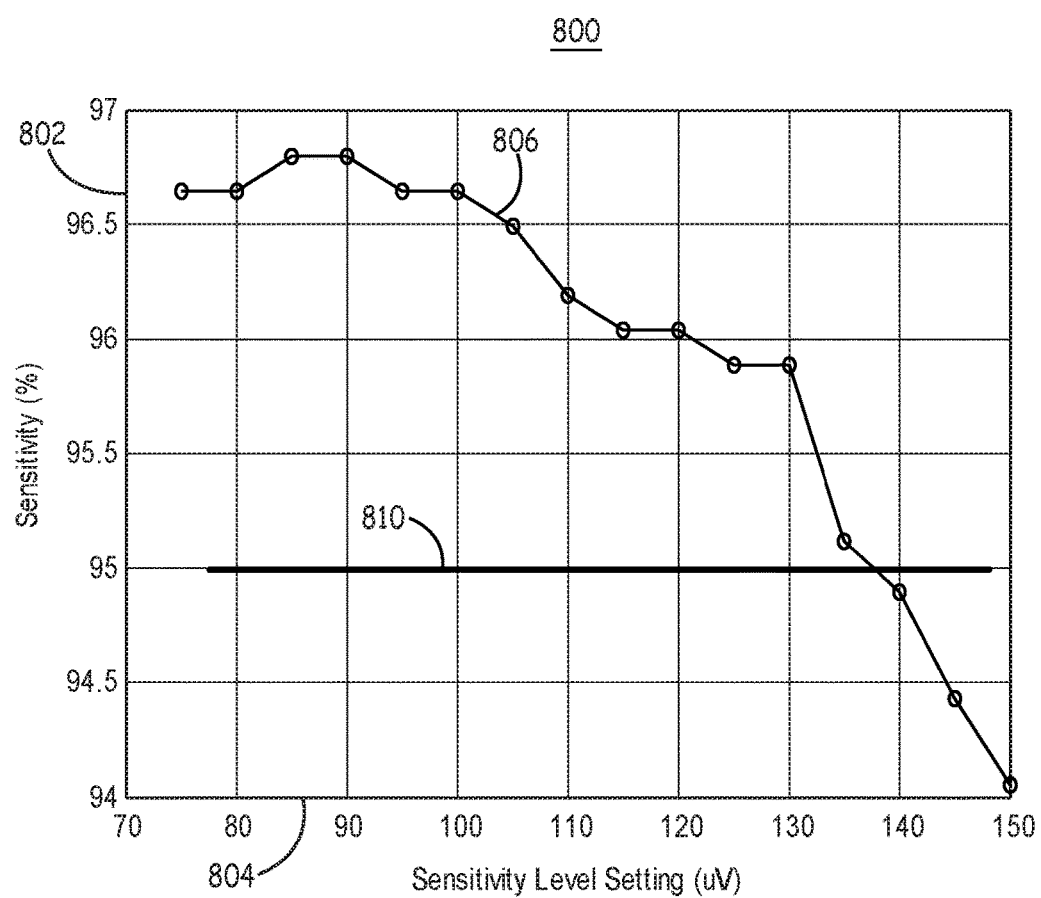
FIG. 13 is a plot of a VT/VF detection sensitivity curve as a function of the programmed sensitivity setting.

FIG. 13 is a plot 800 of an example VT/VF detection sensitivity curve 806 as a function of the programmed sensitivity setting 804. When programmed sensitivity setting is less than approximately 135 microvolts, the VT/VF detection sensitivity is greater than the alert threshold 810, shown as 95% in this example though other alert threshold levels may be selected. In this example, when the programmed sensitivity setting is 140 microvolts or higher, the VT/VF detection sensitivity falls below the alert threshold 810, and the ICD system 10 may generate an alert displayed on external device display 54 as described below in response to a sensitivity setting greater than 140 microvolts being selected for programming.

FIGS. 12 and 13 represent VT/VF detection sensitivity as a function of a single sensing threshold control parameter setting. It is recognized that instead of a single parameter function as shown in FIG. 12, VT/VF sensitivity may be modeled in a multi-parameter, n-dimensional model taking into account a combination of sensing threshold parameters. Furthermore, it is contemplated that instead of sensitivity or in addition to sensitivity, VT/VF detection specificity may be modeled for one or more sensing threshold parameters, individually or in a multi-parameter, n-dimensional model. Sensing threshold control parameters may be determined based on baseline cardiac electrical signal features and selected in order to achieve a targeted specificity and/or targeted sensitivity.

Returning to FIG. 11, at block 604, a processor included in control circuit 80 may determine baseline cardiac signal features. During a confirmed normal sinus rhythm, for example, one or more of the R-wave amplitude, R-wave width, T-wave amplitude, P-wave amplitude, R-T time interval, R-P time interval, T-P time interval, and/or baseline noise may be determined. The R-T, R-P and T-P time intervals may be determined as time intervals between the absolute maximum peak amplitude of the respective R-, T- and P-waves or between other predefined fiducial points of these waves. The normal sinus rhythm may be confirmed manually or based on R-R intervals being greater than a tachyarrhythmia detection interval, no cardiac pacing being delivered, and/or an R-wave morphology match score greater than a predetermined threshold. The cardiac signal features may be determined by control circuit 80 from a digitized, filtered and rectified cardiac signal received from sensing circuit 86.

Alternatively, cardiac signal features may be determined manually from a cardiac electrical signal transmitted to and displayed by external device 40 or determined automatically by external device processor 52 from the transmitted cardiac electrical signal. The cardiac signal feature values may then be used by external device processor 52 for determining recommended R-wave sensing threshold control parameters or the cardiac signal feature values may be programmed into ICD 14, stored in ICD memory 82, and retrieved by a processor included in control circuit 80 for use in determining R-wave sensing threshold control parameters.

With continued reference to FIG. 5, at block 606 of FIG. 11, a processor of control circuit 80 may determine control parameters for setting the starting value 116 of the R-wave sensing threshold. As described above in conjunction with FIG. 7, a variable gain applied to the sensitivity setting for determining a maximum R-wave sensing threshold limit may be determined based on the programmed sensitivity setting. The maximum R-wave sensing threshold limit is one control parameter used to determine the starting value 116. Another control parameter is the percentage of the maximum peak amplitude 112 of the currently sensed R-wave 104 that is used to determine the starting value 116. This percentage may be based on a T/R ratio of the peak T-wave voltage amplitude to the peak R-wave voltage amplitude 112 determined from the filtered, rectified cardiac electrical signal at block 604. For example, if the T/R ratio is 0.5, the starting R-wave sensing threshold may be determined as at least 0.6 or 0.7 of the maximum peak R-wave amplitude 112 or a percentage of at least 60% or 70%. If the T/R ratio is 0.3, the percentage may be set to 50% or some other percentage greater than the T/R ratio.

In other examples, a minimum limit of starting value 116 may be set based on the T-wave amplitude determined at block 604, e.g., a minimum limit of the starting value may be determined as a percentage greater than the maximum peak T-wave voltage amplitude, e.g., 125% of the peak T-wave voltage amplitude or 150% of the peak T-wave voltage amplitude, or a fixed interval greater than the peak T-wave voltage amplitude, e.g., 0.25 mV or 0.5 mV greater than the peak T-wave voltage amplitude.

At block 608, control circuit 80 may determine one or more control parameters for use in setting the second threshold value 118 (shown in FIG. 5). The second threshold value 118 may be set as a second percentage of the peak R-wave voltage amplitude 112 that is less than the percentage used to determine the starting value 116. This second percentage may be based on the P/R ratio of the maximum peak P-wave voltage amplitude to the maximum peak R-wave voltage amplitude 112 determined from the filtered, rectified cardiac electrical signal at block 604. For example, if the P/R ratio is 0.2, the second threshold value 118 may be determined as 0.4, or 40%, of the maximum peak R-wave amplitude. If the P/R ratio is 0.3, the percentage may be set to 50% or some other percentage greater than the P/R ratio.

In other examples, a minimum limit of the second threshold value 118 may be set based on the P-wave amplitude determined at block 604. For example, a minimum limit of the second threshold value 118 may be determined as a percentage of the P-wave amplitude, e.g., 125% of the P-wave amplitude or 150% of the P-wave amplitude, or a fixed amount greater than the maximum peak P-wave voltage amplitude, e.g., 0.2 mV or 0.3 mV, or other fixed amount than the peak P-wave amplitude.

At block 610, the control circuit 80 may set the second blanking interval 132 based on an R-wave width determined at block 604. As described previously, the first blanking interval 130 may be a hardware implemented blanking interval that is absolute and may define a minimum possible value of the second blanking interval 132. An R-wave width measurement may be determined at block 604 from a bandpass filtered cardiac electrical signal as the time interval from a fiducial point on the positive-going portion of the R-wave to a fiducial point on the negative-going portion of the R-wave, e.g., from the first positive crossing of a predetermined voltage to the last negative-going crossing of the predetermined voltage or from a maximum +dV/dt to a maximum −dV/dt. The second blanking interval 132 may be set to be at least equal to the determined R-wave width, a pre-determined portion of the R-wave width, or a fixed interval greater than or less than the R-wave width. The manner in which the second blanking interval 132 is determined based on an R-wave width may depend on how the R-wave width is determined. Example methods for determining an R-wave width are generally disclosed in U.S. Pat. No. 8,983,586 (Zhang) and U.S. Pat. No. 5,312,441 (Mader, et al.), both patents incorporated herein by reference in their entirety.

At block 612, control circuit 80 may determine the sense delay interval 134 based on the R-T interval determined at block 604. For example, sense delay interval 134 may be a fixed interval longer than the R-T interval, e.g., 20 ms longer than the measured R-T interval, or a predetermined percentage of the R-T interval, e.g., 120% of the R-T interval.

The drop time interval 136 may be determined by control circuit 80 at block 614 based on the R-P interval determined at block 604, e.g., as a fixed interval or percentage greater than the R-P interval. Since the R-T and R-P intervals may change with heart rate, the control circuit 80 may adjust the sense delay interval 134 and the drop time interval 136 based on heart rate (e.g., based on a running average of a predetermined number of recent RR intervals) in addition to or alternatively to basing the values on the measured R-T and R-P intervals.

The programmed sensitivity setting may be determined and set at block 615 based on the P-wave amplitude and/or baseline noise determined at block 604. A baseline noise amplitude may be determined by measuring the peak cardiac signal amplitude during a baseline window set between cardiac events, e.g., after the T-wave and before an R-wave. The sensitivity setting may be determined as the lowest setting that is greater than the determined baseline noise amplitude or a fixed interval or percentage greater than the determined baseline noise amplitude.

At block 616, control circuit 80 may be configured to compare the R-wave sensing threshold control parameters to the population-based VT/VF detection sensitivity data stored at block 602. The R-wave sensing threshold control parameters may include a combination of automatically determined control parameters set by control circuit 80 as described above and/or user-programmed control parameters. Individual control parameter settings or combinations of control parameter settings may be compared to VT/VF detection sensitivity data to predict the expected sensitivity for detecting VT and VF when the currently selected R-wave sensing threshold control parameters are utilized.

If any of the control parameters, individually or in combination, result in an expected VT/VF detection sensitivity that is less than the alert threshold (e.g., threshold 710 in FIG. 12), an alert condition is detected at block 618. In response to detecting an alert condition, control circuit 80 may generate an alert notification at block 620 that is transmitted to external device 40 and displayed on user display 54. A user may then review the programmed settings and make any adjustments needed to improve the expected VT/VF detection sensitivity or accept the programmed settings without adjustments. The programmed settings with any adjustments may be transmitted back to ICD 14 and stored in memory 82 at block 622 for use in controlling the R-wave sensing threshold.

In some examples, detection sensitivity data are stored in memory 82 of ICD 14 and the process of flow chart 600 is performed automatically by control circuit 80 for setting the sensing threshold control parameters. A targeted VT/VF detection sensitivity value may be programmed into ICD 14 by a user and ICD 14 may determine the sensing threshold control parameters based on the targeted sensitivity and the baseline cardiac signal features. This process may be repeated periodically for updating the sensing threshold control parameters.

In other examples, the VT/VF detection sensitivity data stored at block 602 is stored in memory 53 of external device 40. The operations of blocks 604 through 618 may be performed by a processor included in control circuit 80, by external device processor 52 after receiving a cardiac electrical signal episode from ICD 14 via ICD telemetry circuit 88 and external device telemetry unit 58, or cooperatively by a processor of control circuit 80 and external device processor 52 with some steps or operations performed by control circuit 80 and some performed by processor 52. Processor 52 may perform the comparison at block 616 and generate the display of the alert notification at block 620 on display 54 in response to detecting an alert condition at block 618. Upon user acceptance of the programmed settings of the R-wave sensing threshold control parameters, after any adjustments made based on an alert if generated, external device 40 transmits the programmable control parameter settings to ICD 14.

Thus, a method and apparatus for controlling R-wave sensing threshold in an extra-cardiovascular ICD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A system comprising an implantable medical device for sensing cardiac electrical events, the system comprising:
   a sensing circuit configured to:
      receive a cardiac electrical signal from electrodes coupled to the implantable medical device;
      sense a plurality of cardiac events, each one of the plurality of cardiac events attendant to a myocardial depolarization and sensed in response to the cardiac electrical signal crossing a cardiac event sensing threshold; and
      after each sensed cardiac event, adjust the cardiac event sensing threshold to a starting threshold value for sensing a next one of the plurality of cardiac events;
   a control circuit configured to:
      determine a gain based on a minimum threshold value;
      determine a maximum limit of the starting threshold value based on the gain and the minimum threshold value of the cardiac event sensing threshold;
      control the sensing circuit to set the starting value of the cardiac event sensing threshold after each sensed cardiac event to be equal to or less than the maximum limit; and
      detect an arrhythmia based on the plurality of cardiac events sensed by the sensing circuit; and
   a therapy delivery circuit configured to generate and deliver an electrical stimulation therapy to a patient's heart via the electrodes coupled to the implantable medical device in response to the control circuit detecting the arrhythmia.

2. The system of claim 1, wherein the minimum threshold value is a programmed sensitivity setting of the sensing circuit and the control circuit is configured to determine the gain by determining an inverse proportion of the programmed sensitivity setting.

3. The system of claim 1, wherein the control circuit is configured to:
   determine a peak amplitude of the sensed cardiac event,
   determine a first threshold value as a first percentage of the peak amplitude; and
   control the sensing circuit to set a next starting threshold value of the cardiac event sensing threshold as a lower one of the first threshold value and the maximum sensing threshold limit.

4. The system of claim 1, wherein the control circuit is configured to:
   set a first blanking interval upon sensing the cardiac event by the sensing circuit;
   set a second blanking interval upon sensing the cardiac event by the sensing circuit;
   determine a peak amplitude of the sensed cardiac event during the first blanking interval;
   determine a threshold value based on the peak amplitude;
   enable the sensing circuit to set a next starting value of the R-wave sensing threshold to a lowest one of the threshold value and the maximum threshold limit at the expiration of the second blanking interval.

5. The system of claim 4, comprising a hardware circuit for setting the first blanking interval and a memory storing firmware for setting the second blanking interval as a programmable interval.

6. The system of claim 1, further comprising a memory storing a look-up table comprising a unique value for the gain for each one of a plurality of programmable minimum threshold values;
   wherein the control circuit is configured to determine the gain based on the minimum threshold value by:
      determining a currently programmed minimum threshold value; and
      retrieving the unique value for the gain stored for the currently programmed minimum threshold value from the look-up table.

7. The system of claim 1, wherein the minimum threshold value is a programmable value and the control circuit is configured to determine the gain as a constant added to a coefficient divided by the minimum threshold value, where the constant and the coefficient are greater than zero.

8. The system of claim 1, wherein the control circuit is further configured to control the sensing circuit to:
   hold the cardiac event sensing threshold at the starting value for a sense delay interval;
   adjust the cardiac event sensing threshold to a second threshold value upon expiration of the sense delay interval;
   hold the cardiac event sensing threshold at the second threshold value for a drop time interval; and
   adjust the cardiac event sensing threshold from the second threshold value to the minimum threshold value upon expiration of the drop time interval.

9. The system of claim 8, wherein the control circuit is configured to control the sensing circuit to set the sense delay interval to a programmed tachyarrhythmia detection interval.

10. The system of claim 8, wherein the control circuit is further configured to control the sensing circuit to increase the cardiac event sensing threshold from the minimum threshold value to a third threshold value greater than the minimum threshold value upon expiration of a maximum sensitivity time interval after expiration of the drop time interval.

11. The system of claim 2, wherein the programmed sensitivity setting is up to one half of a sensitivity setting tested to successfully detect induced ventricular fibrillation.

12. The system of claim 1, further comprising a processor configured to:
   determine a baseline feature from the cardiac electrical signal; and
   set a sensing threshold control parameter to a value based on the feature;

wherein the sensing circuit is configured to adjust the cardiac event sensing threshold according to the control parameter.

13. The system of claim 12, further comprising:
a memory storing tachyarrhythmia detection sensitivity data;
wherein the processor is configured to:
determine an expected tachyarrhythmia detection sensitivity for the control parameter value from the stored tachyarrhythmia detection sensitivity data; and
generate an alert in response to the tachyarrhythmia detection sensitivity being below an alert threshold for the control parameter value.

14. The system of claim 1, wherein the implantable medical device is an implantable cardioverter defibrillator and the electrodes are carried by an extra-cardiovascular lead.

15. A method performed by a system comprising an implantable medical device for sensing cardiac electrical signals, comprising:
receiving a cardiac electrical signal by a sensing circuit of the implantable medical device via electrodes coupled to the implantable medical device;
setting a cardiac event sensing threshold to a starting threshold value;
sensing a cardiac event attendant to a myocardial depolarization in response to the cardiac electrical signal crossing the cardiac event sensing threshold;
detecting an arrhythmia based on a plurality of cardiac events sensed by the sensing circuit; and
generating and delivering an electrical stimulation therapy by a therapy delivery circuit in response to detecting the arrhythmia,
wherein setting the starting threshold value comprises:
determining by a control circuit of the implantable medical device a gain based on a minimum threshold value of the cardiac event sensing threshold;
determining a maximum limit of the starting threshold value based on the gain and the minimum threshold value; and
setting the starting value of the cardiac event sensing threshold to be equal to or less than the maximum limit.

16. The method of claim 15, wherein the minimum threshold value is a programmed sensitivity setting of the sensing circuit and determining the gain comprises determining an inverse proportion of the programmed sensitivity setting.

17. The method of claim 15, further comprising:
determining a peak amplitude of the sensed cardiac event,
determining a first threshold value as a first percentage of the peak amplitude; and
controlling the sensing circuit to set a next starting threshold value of the cardiac event sensing threshold as a lower one of the first threshold value and the maximum sensing threshold limit.

18. The method of claim 15, further comprising:
setting a first blanking interval upon sensing the cardiac event by the sensing circuit;
setting a second blanking interval upon sensing the cardiac event by the sensing circuit;
determining a peak amplitude of the sensed cardiac event during the first blanking interval;
determining a threshold value based on the peak amplitude;

enabling the sensing circuit to set a next starting value of the R-wave sensing threshold to a lowest one of the threshold value and the maximum threshold limit at the expiration of the second blanking interval.

19. The method of claim 18, further comprising setting the first blanking interval by a hardware circuit and setting the second blanking interval as a programmable interval by firmware stored in a memory of the implantable medical device system.

20. The method of claim 15, further comprising:
storing a look-up table in a memory of the implantable medical device, the look-up table comprising a unique value for the gain for each one of a plurality of programmable minimum threshold values; and
determining the gain based on the minimum threshold value by determining a currently programmed minimum threshold value and retrieving the unique value for the gain stored for the currently programmed minimum threshold value from the look-up table.

21. The method of claim 15, wherein the minimum threshold value is a programmable value and the control circuit is configured to determine the gain as a constant added to a coefficient divided by the minimum threshold value, where the constant and the coefficient are greater than zero.

22. The method of claim 15, further comprising:
holding the cardiac event sensing threshold at the starting value for a sense delay interval;
adjusting the cardiac event sensing threshold to a second threshold value upon expiration of the sense delay interval;
holding the cardiac event sensing threshold at the second threshold value for a drop time interval; and
adjusting the cardiac event sensing threshold from the second threshold value to the minimum threshold value upon expiration of the drop time interval.

23. The method of claim 22, further comprising setting the sense delay interval to a programmed tachyarrhythmia detection interval.

24. The method of claim 22, further comprising increasing the cardiac event sensing threshold from the minimum threshold value to a third threshold value greater than the minimum threshold value upon expiration of a maximum sensitivity time interval after expiration of the drop time interval.

25. The method of claim 16, wherein the programmed sensitivity setting is up to one half of a sensitivity setting tested to successfully detect induced ventricular fibrillation.

26. The method of claim 15, further comprising:
determining a baseline feature from the cardiac electrical signal; and
setting a sensing threshold control parameter to a value based on the feature; and
adjusting the cardiac event sensing threshold according to the control parameter.

27. The method of claim 26, further comprising:
storing tachyarrhythmia detection sensitivity data in a memory of the system;
determining an expected tachyarrhythmia detection sensitivity for the control parameter value from the stored tachyarrhythmia detection sensitivity data; and
generating an alert in response to the expected tachyarrhythmia detection sensitivity being below an alert threshold for the control parameter value.

28. The method of claim 15, further comprising:
receiving the cardiac electrical signal by a sensing circuit of the implantable medical device via electrodes carried by an extra-cardiovascular lead coupled to the implantable medical device, wherein the implantable medical device is an implantable cardioverter defibrillator.

29. A non-transitory, computer-readable storage medium comprising a set of instructions which, when executed by processor of an implantable medical device system, cause the system to:
set a cardiac event sensing threshold to a starting threshold value;
sense a cardiac event attendant to a myocardial depolarization by a sensing circuit of the implantable medical device in response to a cardiac electrical signal crossing the cardiac event sensing threshold;
detect an arrhythmia based on a plurality of cardiac events sensed by the sensing circuit; and
generate and deliver an electrical stimulation therapy by a therapy delivery circuit of the implantable medical device in response to detecting the arrhythmia,
wherein setting the cardiac event sensing threshold to the starting threshold value comprises:
determining a gain based on a minimum threshold value of the cardiac event sensing threshold;
determining a maximum limit of the starting threshold value based on the gain and the minimum threshold value; and
setting the starting value of the cardiac event sensing threshold to be equal to or less than the maximum limit.

* * * * *